United States Patent [19]

Heyneker

[11] Patent Number: 5,147,643
[45] Date of Patent: Sep. 15, 1992

[54] DNA SEQUENCES ENCODING HUMAN T-PA SUBSTITUTED AT POSITION 275 OR AT POSITIONS 275 AND 277 AND PHARMACEUTICAL COMPOSITIONS

[75] Inventor: Herbert L. Heyneker, Hillsborough, Gordon A. Vehar, San Carlos, both of Calif.

[73] Assignee: Genentech, Inc., South San Francisco, Calif.

[21] Appl. No.: 741,120

[22] Filed: Aug. 5, 1991

Related U.S. Application Data

[60] Division of Ser. No. 522,480, May 11, 1990, Pat. No. 5,073,494, which is a continuation of Ser. No. 186,494, Apr. 26, 1988, abandoned, which is a continuation of Ser. No. 71,506, Jul. 9, 1987, abandoned, which is a continuation of Ser. No. 846,697, Apr. 1, 1986, abandoned, which is a continuation of Ser. No. 725,468, Apr. 22, 1985, abandoned.

[51] Int. Cl.[5] .................. A61K 32/547; C12P 21/02; C12N 15/58; C12N 9/48
[52] U.S. Cl. .............................. 424/94.64; 435/240.2; 435/252.3; 435/320.1; 536/27; 424/94.63
[58] Field of Search .................. 435/226, 320.1, 252.3, 435/240.2; 536/27; 424/94.63, 94.64

[56] References Cited

U.S. PATENT DOCUMENTS 4,753,879  6/1988  Rosa et al. .......................... 435/212

FOREIGN PATENT DOCUMENTS 0233013  8/1987  European Pat. Off. .
87/04722 8/1987  World Int. Prop. O. .

OTHER PUBLICATIONS

Pennica, D., et al., *Nature*, vol. 301, pp. 214–221, 1983.
Tate, K., et al., *Biochemistry*, vol. 26, pp. 338–343, 1987.

*Primary Examiner*—David L. Lacey
*Assistant Examiner*—Marianne Porta Allen
*Attorney, Agent, or Firm*—Walter H. Dreger

[57] ABSTRACT

Biologically active mutant tissue plasminogen activators are disclosed wherein site directed mutagenesis, for example, of a two-chain activation site renders the mutants resistant to conversion to the two-chain form.

16 Claims, 20 Drawing Sheets

```
GTTCTGAGCACAGGGCTGGAGAGAAAACCTCTGCGAGGAAAGGGAAGGAGCAAGCCGTGA
```

```
                                          -35              -30
                                          met asp ala met lys arg gly leu
ATTTAAGGGACGCTGTGAAGCAATC                 ATG GAT GCA ATG AAG AGA GGG CTC
```

```
            -20
cys cys val leu leu leu cys gly ala val phe val ser pro ser
TGC TGT GTG CTG CTG CTG TGT GGA GCA GTC TTC GTT TCG CCC AGC
```

```
    -10                                          1
gln glu ile his ala arg phe arg arg gly ala arg SER TYR GLN
CAG GAA ATC CAT GCC CGA TTC AGA AGA GGA GCC AGA TCT TAC CAA
```

```
                            10
VAL ILE CYS ARG ASP GLU LYS THR GLN MET ILE TYR GLN GLN HIS
GTG ATC TGC AGA GAT GAA AAA ACG CAG ATG ATA TAC CAG CAA CAT
```

```
    20                                      30
GLN SER TRP LEU ARG PRO VAL LEU ARG SER ASN ARG VAL GLU TYR
CAG TCA TGG CTG CGC CCT GTG CTC AGA AGC AAC CGG GTG GAA TAT
```

```
                        40
CYS TRP CYS ASN SER GLY ARG ALA GLN CYS HIS SER VAL PRO VAL
TGC TGG TGC AAC AGT GGC AGG GCA CAG TGC CAC TCA GTG CCT GTC
```

```
    50                                      60
LYS SER CYS SER GLU PRO ARG CYS PHE ASN GLY GLY THR CYS GLN
AAA AGT TGC AGC GAG CCA AGG TGT TTC AAC GGG GGC ACC TGC CAG
```

```
                    70
GLN ALA LEU TYR PHE SER ASP PHE VAL CYS GLN CYS PRO GLU GLY
CAG GCC CTG TAC TTC TCA GAT TTC GTG TGC CAG TGC CCC GAA GGA
```

```
    80                                      90
PHE ALA GLY LYS CYS CYS GLU ILE ASP THR ARG ALA THR CYS TYR
TTT GCT GGG AAG TGC TGT GAA ATA GAT ACC AGG GCC ACG TGC TAC
```

```
                    100
GLU ASP GLN GLY ILE SER TYR ARG GLY THR TRP SER THR ALA GLU
GAG GAC CAG GGC ATC AGC TAC AGG GGC ACG TGG AGC ACA GCG GAG
```

```
    110                                     120
SER GLY ALA GLU CYS THR ASN TRP ASN SER SER ALA LEU ALA GLN
AGT GGC GCC GAG TGC ACC AAC TGG AAC AGC AGC GCG TTG GCC CAG
```

```
                    130
LYS PRO TYR SER GLY ARG ARG PRO ASP ALA ILE ARG LEU GLY LEU
AAG CCC TAC AGC GGG CGG AGG CCA GAC GCC ATC AGG CTG GGC CTG
```

```
    140                                     150
GLY ASN HIS ASN TYR CYS ARG ASN PRO ASP ARG ASP SER LYS PRO
GGG AAC CAC AAC TAC TGC AGA AAC CCA GAT CGA GAC TCA AAG CCC
```

```
                    160
TRP CYS TYR VAL PHE LYS ALA GLY LYS TYR SER SER GLU PHE CYS
TGG TGC TAC GTC TTT AAG GCG GGG AAG TAC AGC TCA GAG TTC TGC
```

```
    170                                     180
SER THR PRO ALA CYS SER GLU GLY ASN SER ASP CYS TYR PHE GLY
AGC ACC CCT GCC TGC TCT GAG GGA AAC AGT GAC TGC TAC TTT GGG
```

FIG. 2A

```
                              190
ASN GLY SER ALA TYR ARG GLY THR HIS SER LEU THR GLU SER GLY
AAT GGG TCA GCC TAC CGT GGC ACG CAC AGC CTC ACC GAG TCG GGT 200                                         210
ALA SER CYS LEU PRO TRP ASN SER MET ILE LEU ILE GLY LYS VAL
GCC TCC TGC CTC CCG TGG AAT TCC ATG ATC CTG ATA GGC AAG GTT

220
TYR THR ALA GLN ASN PRO SER ALA GLN ALA LEU GLY LEU GLY LYS
TAC ACA GCA CAG AAC CCC AGT GCC CAG GCA CTG GGC CTG GGC AAA 230                                         240
HIS ASN TYR CYS ARG ASN PRO ASP GLY ASP ALA LYS PRO TRP CYS
CAT AAT TAC TGC CGG AAT CCT GAT GGG GAT GCC AAG CCC TGG TGC

250
HIS VAL LEU LYS ASN ARG ARG LEU THR TRP GLU TYR CYS ASP VAL
CAC GTG CTG AAG AAC CGC AGG CTG ACG TGG GAG TAC TGT GAT GTG 260                                         270
PRO SER CYS SER THR CYS GLY LEU ARG GLN TYR SER GLN PRO GLN
CCC TCC TGC TCC ACC TGC GGC CTG AGA CAG TAC AGC CAG CCT CAG

280
PHE ARG ILE LYS GLY GLY LEU PHE ALA ASP ILE ALA SER HIS PRO
TTT CGC ATC AAA GGA GGG CTC TTC GCC GAC ATC GCC TCC CAC CCC 290                                         300
TRP GLN ALA ALA ILE PHE ALA LYS HIS ARG ARG SER PRO GLY GLU
TGG CAG GCT GCC ATC TTT GCC AAG CAC AGG AGG TCG CCC GGA GAG

310
ARG PHE LEU CYS GLY GLY ILE LEU ILE SER SER CYS TRP ILE LEU
CGG TTC CTG TGC GGG GGC ATA CTC ATC AGC TCC TGC TGG ATT CTC 320                                         330
SER ALA ALA HIS CYS PHE GLN GLU ARG PHE PRO PRO HIS HIS LEU
TCT GCC GCC CAC TGC TTC CAG GAG AGG TTT CCG CCC CAC CAC CTG

340
THR VAL ILE LEU GLY ARG THR TYR ARG VAL VAL PRO GLY GLU GLU
ACG GTG ATC TTG GGC AGA ACA TAC CGG GTG GTC CCT GGC GAG GAG 350                                         360
GLU GLN LYS PHE GLU VAL GLU LYS TYR ILE VAL HIS LYS GLU PHE
GAG CAG AAA TTT GAA GTC GAA AAA TAC ATT GTC CAT AAG GAA TTC

370
ASP ASP ASP THR TYR ASP ASN ASP ILE ALA LEU LEU GLN LEU LYS
GAT GAT GAC ACT TAC GAC AAT GAC ATT GCG CTG CTG CAG CTG AAA 380                                         390
SER ASP SER SER ARG CYS ALA GLN GLU SER SER VAL VAL ARG THR
TCG GAT TCG TCC CGC TGT GCC CAG GAG AGC AGC GTG GTC CGC ACT

400
VAL CYS LEU PRO PRO ALA ASP LEU GLN LEU PRO ASP TRP THR GLU
GTG TGC CTT CCC CCG GCG GAC CTG CAG CTG CCG GAC TGG ACG GAG 410                                         420
CYS GLU LEU SER GLY TYR GLY LYS HIS GLU ALA LEU SER PRO PHE
TGT GAG CTC TCC GGC TAC GGC AAG CAT GAG GCC TTG TCT CCT TTC
```

FIG. 2B

```
                                   430
TYR SER GLU ARG LEU LYS GLU ALA HIS VAL ARG LEU TYR PRO SER
TAT TCG GAG CGG CTG AAG GAG GCT CAT GTC AGA CTG TAC CCA TCC 440                                  450
SER ARG CYS THR SER GLN HIS LEU LEU ASN ARG THR VAL THR ASP
AGC CGC TGC ACA TCA CAA CAT TTA CTT AAC AGA ACA GTC ACC GAC

460
ASN MET LEU CYS ALA GLY ASP THR ARG SER GLY GLY PRO GLN ALA
AAC ATG CTG TGT GCT GGA GAC ACT CGG AGC GGC GGG CCC CAG GCA 470                                  480
ASN LEU HIS ASP ALA CYS GLN GLY ASP SER GLY GLY PRO LEU VAL
AAC TTG CAC GAC GCC TGC CAG GGC GAT TCG GGA GGC CCC CTG GTG

490
CYS LEU ASN ASP GLY ARG MET THR LEU VAL GLY ILE ILE SER TRP
TGT CTG AAC GAT GGC CGC ATG ACT TTG GTG GGC ATC ATC AGC TGG 500                                  510
GLY LEU GLY CYS GLY GLN LYS ASP VAL PRO GLY VAL TYR THR LYS
GGC CTG GGC TGT GGA CAG AAG GAT GTC CCG GGT GTG TAC ACC AAG 520                    527
VAL THR ASN TYR LEU ASP TRP ILE ARG ASP ASN MET ARG PRO OP
GTT ACC AAC TAC CTA GAC TGG ATT CGT GAC AAC ATG CGA CCG TGA
```

CCAGGAACACCCGACTCCTCAAAAGCAAATGAGATCCCGCCTCTTCTTCTTCAGAAGACA

CTGCAAAGGCGCAGTGCTTCTCTACAGACTTCTCCAGACCCACCACACCGCAGAAGCGGG

ACGAGACCCTACAGGAGAGGGAAGAGTGCATTTTCCCAGATACTTCCCATTTTGGAAGT

TTTCAGGACTTGGTCTGATTTCAGGATACTCTGTCAGATGGGAAGACATGAATGCACACT

AGCCTCTCCAGGAATGCCTCCTCCCTGGGCAGAAAGTGGCCATGCCACCCTGTTTTCAGCTA

AAGCCCAACCTCCTGACCTGTCACCGTGAGCAGCTTTGGAAACAGGACCACAAAAATGAA

AGCATGTCTCAATAGTAAAAGATAACAAGATCTTTCAGGAAAGACGGATTGCATTAGAA

ATAGACAGTATATTTATAGTCACAAGAGCCCAGCAGGGCCTCAAAGTTGGGGCAGGCTGGC

TGGCCCGTCATGTTCCTCAAAAGCACCCTTGACGTCAAGTCTCCTTCCCCTTTCCCCACT

CCCTGGCTCTCAGAAGGTATTCCTTTTGTGTACAGTGTGTAAAGTGTAAATCCTTTTTCT

TTATAAACTTTAGAGTAGCATGAGAGAATTGTATCATTTGAACAACTAGGCTTCAGCATA

TTTATAGCAATCCATGTTAGTTTTTACTTTCTGTTGCCACAACCCTGTTTTATACTGTA

CTTAATAAATTCAGATATATTTTTCACAGTTTTTCCAAAAAAAAAAAAAA

FIG. 2C

TIME (Min)

DNA SEQUENCES ENCODING HUMAN T-PA SUBSTITUTED AT POSITION 275 OR AT POSITIONS 275 AND 277 AND PHARMACEUTICAL COMPOSITIONS

This is a divisional application under 35 U.S.C. § 120/121 of application Ser. No. 07/522,480 filed May 11, 1990, now U.S. Pat. No. 5,073,494, which is a continuing application of Ser. No. 07/186,494 filed Apr. 26, 1988, abandoned, which is a continuing application of serial number 07/071,506 filed Jul. 9, 1987, abandoned, which is a continuation of Ser. No. 06/846,697 filed Apr. 1, 1986, abandoned, which is a continuation of Ser. No. 06/725,468 filed Apr. 22, 1985, abandoned.

FIELD OF THE INVENTION

The present invention is directed to particular novel mutants of human tissue plasminogen activator (t-PA). These mutants, although embraced generically by earlier disclosure, as noted infra, are novel, specific derivatives which exhibit activities which defied prediction from the prior research of others on the basic human tissue plasminogen activator molecule or the model serine proteases trypsin and chymotrypsin.

BACKGROUND OF THE INVENTION

Human tissue plasminogen activator was first identified as a substantially pure isolate from a natural source, and tested for requisite plasminogen activator activity by Collen, et al. European Patent Application Publication No. 041766, published Dec. 16, 1981, based upon a first filing of Jun. 11, 1980.

Subsequently, researchers in Assignee's laboratories produced human tissue plasminogen activator, essentially free of proteins with which it is ordinarily associated, via recombinant DNA technology. This work has been recorded in the scientific literature and in European Patent Application Publication No. 093619 published Nov. 9, 1983, based upon a first filing on May 5, 1982. The above patent application (EPO Publication No. 093619) contemplates the production of various human plasminogen activator derivatives, variously modified by amino acid substitutions, deletions, additions, or replacements prepared, for example, by site directed mutagenesis of the underlying DNA.

As disclosed therein, human tissue plasminogen activator (t-PA) exists in both a single-chain and a two-chain form. The latter is a proteolytic derivative of the former. It has been shown that proteolytic conversion of the single-chain form to the two-chain form occurs during the lysis of a fibrin clot. Rijken, et al. *J. Biol. Chem.* 257, 2920 (1982). It is believed that the two-chain form is the agent responsible for plasminogen activator activity, although there have been some initial reports indicating that the single-chain form of human t-PA, Rijken, Ibid, and the single-chain form of porcine t-PA, Ranby, et al. *Thromb. Res.* 27, 176 (1982), may have some activity. See also Rijken et al., *Biochim. Biophy. Acta* 580 (1979).

Subsequent investigators, however, have dismissed such reports of single-chain activity as being the result of contamination of these preparations with low amounts of the two-chain form. Andreasen, et al. *EMBO J.* 3, 51 (1984); Ichinose, et al. *FEBS. Letters* 175, 412 (1984). Such subsequent reports have reaffirmed the general belief that serine proteases, including t-PA, are expressed as inactive, single-chain zymogens which only become active upon hydrolysis of the protein at a specific site, e.g., arginine at position 275 in the case of t-PA.

In vivo comparisons of the ability of one-chain verses two-chain plasminogen activator to lyse fibrin clots have been performed using rabbits and dogs. In rabbits, approximately equal potency has been observed for the two forms of this enzyme. Collen et al., *J. Clin. Invest.* 71, 368 (1983). When evaluated in a similar model in dogs, however, the one-chain form of plasminogen activator was reported to be slightly less active than the two-chain form. Korninger et al., *J. Clin. Invest.* 69, 573 (1982). These studies, therefore, indicate that one-chain plasminogen activator is no better than, and in fact may be less potent than, the two-chain form of plasminogen activator in their ability to dissolve fibrin clots in vivo.

SUMMARY OF THE INVENTION

The present application is directed to novel mutants of human t-PA, which surprisingly exhibit activity on par with or better than the human t-PA first isolated by Collen, et al. (EPO Publication No. 041766), as well as the t-PA molecules described in the aforementioned recombinant patent application. (EPO Publication No. 093619). In a particular embodiment, specific mutants covered by the present invention include those having certain amino acid substitutions within the site surrounding positions 275 and 276 of the human t-PA amino acid sequence, occupied respectively by arginine and isoleucine. Certain enzymatically active molecules recognize this (these) site(s) (perhaps together with one or more adjacent amino acids) and functionally hydrolyze the bonds after basic amino acids, particularly between arginine/isoleucine and lysine/glycine, resulting in two-chain material. The two chains remain associated through disulfide bonding via cysteine residues. According to this embodiment of the present invention, for example, the substitution at these positions with amino acids other than, e.g., arginine and lysine, serves to produce mutants wherein the respective cleavage sites are altered such that two-chain human t-PA is not formed in vitro or in vivo, or is formed at a reduced rate. Thus, this aspect of the present invention provides mutagenized single-chain human t-PA for purposes of testing biological activity. It has been found that such mutants are rendered immune, or at least resistant, to hydrolysis at the 275/276 site and that the resultant single-chain human t-PA mutants are unexpectedly on par with the activity of the Collen et al. and/or recombinant t-PA molecules described above, in certain biological assays. Furthermore, indications are that such mutants are less reactive with naturally occurring t-PA inhibitors.

Following more generally from the foregoing summary is contemplated with the present invention imparting the resistance to proteolytic degradation at any site recognized to be susceptible to such including, in addition to the specific most widely recognized site at amino acid site 275/276, the known sites at amino acids 27/28, 40/41 and 462/463.

Focusing with more particularity on the so-called one-chain, two-chain 275/276 site, this proteolytically susceptible cleavage site falls within a region defined by amino acids about 270 to about 279, or more preferably about 275 to about 279. Mutagenesis within this region makes it less, or not at all, susceptible to degradation creating a molecule that remains, with respect to this site, in single-, or one-chain, form. Further, destruction of the site by preferred mutagenesis at position 275, forming for example E275 t-PA, creates a molecule that may be susceptible (albeit at a considerably lower rate) to degradation (cleavage) at the 277/278 site. For this reason, for example, further mutagenesis at the latter site creating, for example, I277 or E275I277 t-PA further protects the one-chain integrity of the molecule. Another embodiment is to modify the amino acid between those two 275/276 and 277/278 sites, namely, amino acid 276 preparing, as examples P276 t-PAs, e.g., P276 t-PA, E275P276 t-PA, P276I277 t-PA, and E275P276I277 t-PA. Further mutagenesis within the about 270 to about 279 region. or any other site, follows from the context of the present invention, the endpoint being measured by the susceptibility of cleavage(s) of the resultant t-PA molecule.

BRIEF DESCRIPTION OF THE DRAWINGS

FIGS. 2A-2C represent the DNA and amino acid sequences of t-PA including 5' and 3' -untranslated regions.

DETAILED DESCRIPTION

Figure 1:
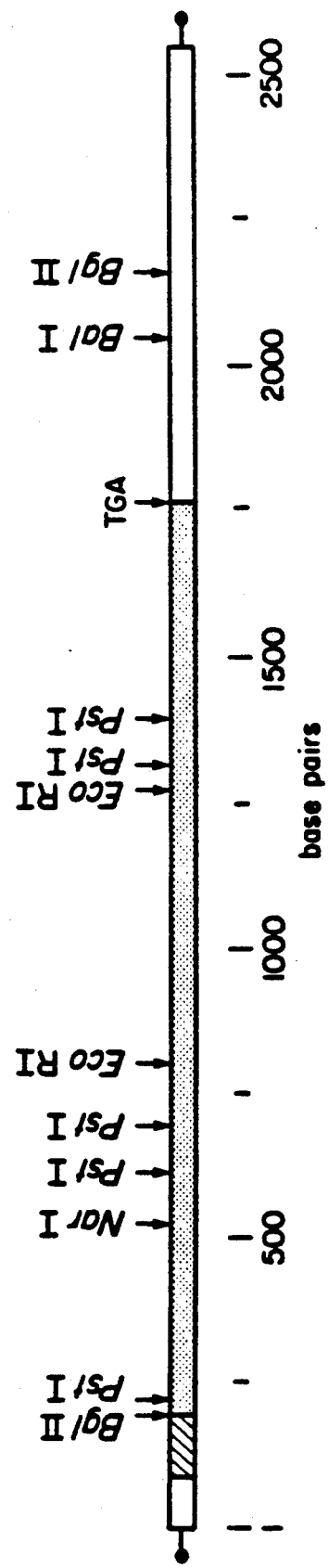
FIG. 1 is a restriction map of the DNA of human t-PA and includes 5' and 3' -untranslated regions as well as sequences encoding pre-t-PA. The speckled area represents the structure gene for t-PA.

As used herein, "human tissue plasminogen activator", "human t-PA", or "t-PA" denotes human extrinsic (tissue-type) plasminogen activator as produced, e.g., by recombinant cell culture systems, in bioactive forms comprising protease portion and corresponding to the plasminogen activator otherwise native to human tissue. It will be understood that natural allelic variations exist and occur from individual to individual, demonstrated by (an) amino acid difference(s) in the overall sequence. In addition, glycosylation patterns will depend on the nature of the host cellular environment.

It seems now clear that the human tissue plasminogen activator molecule contains five domains (stretches of amino acid sequence) that have been defined with reference to homologous or otherwise similar structures identified in various other proteins such as trypsin, chymotrypsin, plasminogen, prothrombin, fibronectin and epidermal growth factor. These domains have been designated, starting at the N-terminus of the amino acid sequence of human tissue plasminogen activator, as 1) the finger region (F) that has variously been defined as including amino acid 1 upwards of about 44, 2) the growth factor region (G) that has been variously defined as stretching from about amino acid 45 upwards of amino acid 91 (based upon its homology with EGF), 3) kringle one (K1) that has been defined as stretching from about amino acid 92 to about 173, 4) kringle two (K2) that has been defined as stretching from about amino acid 180 to about amino acid 261 and 5) the so-called serine protease domain (P) that generally has been defined as stretching from about amino acid 264 to the C-terminal end of the molecule. These domains are situated contiguously generally of one another, or are separated by short "linker" regions, and account for the entire amino acid sequence from about 1 to 527 amino acids in its putative mature form.

Each domain has been described variously as contributing certain specific activity: that is, the finger domain has been variously described as containing a sequence essential or at least of major importance for high binding affinity to fibrin. (This activity is thought important for the high specificity human tissue plasminogen activator displays with respect to clot lysis at the locus of a fibrin rich thrombus.) The growth factor-like region likewise has been associated with cell surface binding activity, at least with respect to urokinase. The Kringle 2 region has also been strongly associated with fibrin binding and with the ability of fibrin to stimulate the activity of t-PA. The serine protease domain seems to enjoy unanimous agreement of being the workhorse domain of the molecule in respect of plasminogen activating activity.

A "two-chain cleavage site" in t-PA comprises at least the arginine residue at position 275. However, various amino acids adjacent to or within several residues of position 275, e.g., up to about 279, are also believed to be a part of the domain recognized by enzymes which convert plasminogen activator to its two-chain form. Thus, replacement of amino acids at positions other than or in addition to 275 within the domain result in mutant plasminogen activators that are resistant to conversion to the two-chain form. See also the discussion supra.

In the particular embodiment, "single-chain plasminogen activator mutant" is a plasminogen activator which is resistant to conversion to the two-chain form. It is characterized by single or multiple amino acid substitutions within the region defining the two-chain activation site. As modified, such activation site is not enzymatically recognized, and therefore, not hydrolyzed by enzymes which normally convert plasminogen activator to its two-chain form.

By analogy to trypsin and chymotrypsin, it is believed that the importance of the formation of the two-chain form of any serine protease is the consequential presence of the free α-amino group in t-PA at position 276. In this comparison. upon cleavage at arg-275, the α-amino group 276 would be free to interact with the polypeptide chain in the area of the active site serine of t-PA. The present invention therefore covers any mutation which would interfere with the interaction of such an α-amino group with the protease active site without diminishing overall activity of the molecule as a whole.

A variety of methods may be used to induce mutations of underlying DNA so as to prepare the mutants hereof. One such method, illustrated herein as a particularly preferred embodiment, comprises first inserting a fragment of the native t-PA gene, containing sequences coding for the region to be mutated, into the replicative form of phage M13mp8 to form M13mp8PA. A synthetic oligonucleotide, complementary to the inserted t-PA sequences but containing one or more nucleotide triplets which code for the amino acid to be substituted, is then annealed to the single stranded form of M13mp8PA to form a double stranded region. This region serves as a primer for DNA polymerase I synthesis of the remaining complementary strand. After replication and identification, the mutant t-PA sequence may be further modified or used to construct a prokaryotic or eukaryotic vector for expressing the mutated t-PA polypeptide.

As mentioned, the above described general method may also be used to mutate t-PA at positions other than the 275/276 and/or 277/278 two-chain cleavage sites, to produce mutated t-PA derivatives falling within the present invention. Such other positions are polypeptide sequences which are susceptible to enzymatic hydrolysis such as trypsin-like cleavage sites which typically comprise arginine or lysine followed by isoleucine, serine, or alanine. Substitution of one or more amino acids within such trypsin-like cleavage site results in mutant t-PAs which resist hydrolysis by trypsin-like proteases. Such resistance to enzymatic degradation during expression and purification as well as during in vivo administration as a pharmaceutical agent results in a t-PA which does not lose biological activity as compared to the non-mutated t-PA. Examples of such trypsin-like cleavage sites within the human t-PA molecule include arginine-alanine (positions 40-41), arginine-serine (positions 27-28), and arginine-serine (positions 462-463).

For purposes of shorthand designation of t-PA variants hereof, it is noted that numbers refer to the amino acid residue/position along the 527 amino acid sequence of putative mature t-PA—see EPA 093619 which corresponds to U.S. Pat. No. 4,766,075. See also FIGS. 2A, 2B and 2C herein. Amino acid identification uses the single letter alphabet of amino acids, i.e.:

| Asp | D | Aspartic acid | Ile | I | Isoleucine |
| Thr | T | Threonine | Leu | L | Leucine |
| Ser | S | Serine | Tyr | Y | Tyrosine |
| Glu | E | Glutamic acid | Phe | F | Phenylalanine |
| Pro | P | Proline | His | H | Histidine |
| Gly | G | Glycine | Lys | K | Lysine |
| Ala | A | Alanine | Arg | R | Arginine |
| Cys | C | Cysteine | Trp | W | Tryptophan |
| Val | V | Valine | Gln | Q | Glutamine |
| Met | M | Methionine | Asn | N | Asparagine | at the number following such single letters refers to the amino acid position, e.g., E275 means a variant hereof having, inter alia, glutamic acid at position 275. Thus, E275I277 t-PA is the variant t-PA hereof having a glutamic acid at position 275 and an isoleucine at position 277.

A. General

Mutated t-PA derivatives hereof are prepared 1) having methionine as its first amino acid (present by virtue of the ATG start signal codon insertion in front of the structural gene) or 2) where the methionine is intra- or extracellularly cleaved, having its normally first amino acid, or 3) together with either its signal polypeptide or conjugated protein other than its conventional signal polypeptide, the signal polypeptide or a conjugate being specifically cleavable in an intra- or extracellular environment, or 4) by direct expression in mature form without the necessity of cleaving away any extraneous, superfluous polypeptide. In all events, the thus produced human mutated t-PA, in its various forms, is recovered and purified to a level suitable for the treatment of various vascular conditions or diseases such as myocardial infarct, strokes, pulmonary embolism, deep vain thrombosis, peripheral arterial occlusion and other thrombotic conditions.

Human mutated t-PA also has a functional definition in being capable of binding to fibrin and of mediating in vivo or in vitro conversion of plasminogen to plasmin which in turn solubilizes fibrin clots.

"Expression Vector" includes vectors which are capable of expressing DNA sequences contained therein, where such sequences are operably linked to other sequences capable of effecting their expression and which are replicable in the host organisms, either as episomes or as an integral part of the chromosomal DNA.

"Recombinant host cells" refers to cells which have been transformed with expression vectors constructed using recombinant DNA techniques.

B. Host Cell Cultures and Vectors

The vectors and method disclosed herein are suitable for use in host cells over a wide range of prokaryotic and eukaryotic organisms. For example, *E. coli* K12 strain 294 (ATCC No. 31446) is particularly useful. Other microbial strains which may be used such as *E. coli* B, and *E. coli* X1776 (ATCC No. 31537). These examples are, of course, intended to be illustrative rather than limiting.

In addition to prokaryotes, eukaryotic organisms, such as yeast cultures, may be used. Cultures of cells derived from multicellular organisms are the hosts of choice currently. In principle, any such cell culture is workable; however, interest has been greatest in cells from vertebrates, and propagation of these cells in culture (tissue culture) has become a repeatable procedure— see *Tissue Culture*, Academic Press, Kruse and Patterson, editors (1973). Examples of such useful host cell lines re VERO and HeLa cells, Chinese Hamster Ovary (CHO) cell lines, e.g., DHFR+ CHO-K1 cells (ATCC No. CCL 61), W138, BHK, COS-7 and MDCK cell lines.

Examples which are set forth hereinbelow describe the use of *E. coli* using the trp promoter system and the use of CHO cells using expression vectors which include the SV40 origin of replication as a promoter. However, it would be well within the skill in the art to use alternative prokaryotic or eukaryotic host cell cultures.

C. Methods Employed

1. Transfection

If cells without formidable cell wall barriers are used as host cells, transfection may be carried out by the calcium phosphate precipitation method as described by Graham et al., *Virology* 52, 546 (1978). However, nuclear injection or protoplast fusion may also be used.

If prokaryotic cells or cells which contain substantial cell wall constructions are used, the preferred method of transfection is via calcium chloride as described by Cohen, et al., *Proc. Natl. Acad. Sci.* (USA) 69, 2110 (1972).

2. Vector Construction

Construction of suitable vectors containing the desired coding and control sequence employ standard ligation techniques known per se. Isolated plasmids or DNA fragments are cleaved, tailored, and re-ligated in the form desired to form the plasmids required.

D. EXAMPLES

1. Construction of M13mp8PABglII For t-PA Mutagenesis

Human t-PA DNA was obtained from plasmids pPADHFR-6 (also designated pETPFR) and pPA2-5E10. The preparation of these two t-PA plasmids is described in EPO Application Publication No. 093619, referred to above and incorporated herein by reference. Superfluously, these two plasmids, per se and in transfected form, have been deposited with the American Type Culture Collection, Rockville, MD., USA as follows: pETPFR-ATCC Nos. 40403 and CRL 9606- and pPA25E10-ATCC Nos. 40401 and 67587.

Plasmid pPA25E10 contains sequences coding for the last 508 amino acids of the t-PA gene and 772 base pairs of the 3' untranslated region. This plasmid was digested with SacI and BglII to produce a 744 base pair fragment which was isolated by standard methods as previously described. As can be seen from the known sequence and restiction map of t-PA in FIGS. 1 and 2, this fragment contains the codons for t-PA amino acids 411 through 527 and includes part of the 3' untranslated region.

Plasmid pPADHFR-6 contains the entire structural gene for t-PA and part of the 3' untranslated region. This plasmid was digested with SacI and BglII to produce a 1,230 base pair fragment which was isolated. This fragment contains codons for the first 410 amino acids of the mature form of t-PA.

These fragments were ligated together using standard methods and digested with BglII. A 1,974 base pair fragment containing codons for the entire mature t-PA sequence plus part of the 3' untranslated region was isolated. Double stranded MI3mp8, (Messing, et al. Third Cleveland Symposium on Macromolecules Recombinant DNA, Editor A. Walton, Elsevier, Amsterdam (1981), p. 143) was digested with BamHI and annealed to the BglII digested t-PA to form M13mp8PABglII. *E. coli* JM 101 cells (ATCC No. 33876) were transformed with the double stranded replicative form of M13mp8PABglII. The single stranded and double stranded (RF) forms of M13mp8PABglII may be isolated from *E. coli* JM 101 cells infected with this phage. The single stranded form was used for the site specific mutagenesis of t-PA.

2. Synthesis of Primers for Site Specific Mutagenesis

The human t-PA structural gene was modified by site specific mutagenesis to express t-PAs with amino acid substitutions at various positions. Synthetic oligonucleotides were prepared such as by the solid phase phosphotriester method of Crea et al., *Proc. Natl. Acad. Sci.* USA 75, 5765 (1978). The following synthetic primers were prepared and used for such site specific mutagenesis:

| | 275 | | | 279 | | |
|---|---|---|---|---|---|---|
| Native Amino Acid Sequence | Pro Gln Phe | Arg (R)* | Ile | Lys (K) | Gly | Gly |
| Native DNA Sequence | G CCT CAG TTT | CGC | ATC | AAA | GGA | G |
| Primer 1B8 | | Gly(G) | | Lys(K) | | |
| DNA Sequence | G CCT CAG TTT | GGT | ATC | AAA | GGA | G |
| Primer 2C9 | | Glu(E) | | Lys(K) | | |
| DNA Sequence | G CCT CAG TTT | GAA | ATC | AAA | GGA | G |
| Primer 4A10 | | Arg(R) | | Ile(I) | | |
| DNA Sequence | G CCT CAG TTT | CGC | ATC | ATC | GGA | G |
| Primer 3A7 | | Gly(G) | | Ile(I) | | |
| DNA Sequence | G CCT CAG TTT | GGT | ATC | ATC | GGA | G |
| Primer 4B3 | | Glu(E) | | Ile(I) | | |
| DNA Sequence | G CCT CAG TTT | GAA | ATC | ATC | GGA | G |

*single letter alphabet of amino acids (supra.)

The amino acid and gene sequence of native t-PA is depicted in the first two lines. The primers have triplets which differ from the native gene sequence at the residue shown. The corresponding amino acid substitution is shown above the triplet coding for that amino acid.

3. Site Specific Mutagenesis

Figure 3:
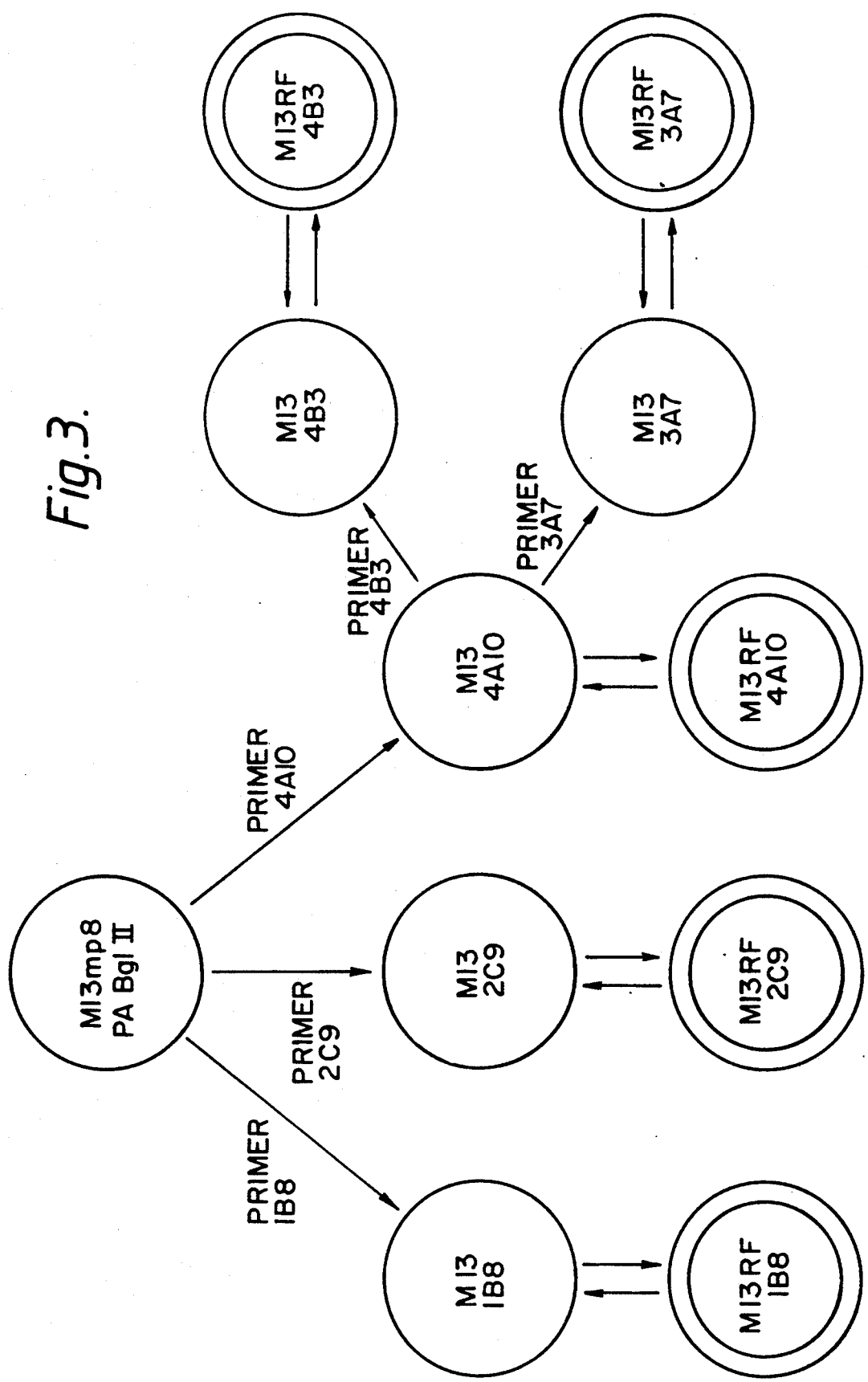
FIG. 3 is the overall scheme used to generate individual clones containing substitutions at position 275.

The procedure described hereinafter, was used to generate different t-PA clones containing the mutated sequence of the synthetic primers. The general method used is that of Adelman, et al. DNA 2 183 (1983), incorporated herein by reference. The overall scheme to generate each of these clones is presented in FIG. 3. M13RF1B8, 3M13RF2C9 and M13RF4A10 were generated by the use of primers containing mutations for the single amino acids shown. Single standard M13RF4A10, containing a mutation at position 277, was annealed with primer 3A7 or 4B3 to generate M13RF3A7 nd M13RF4B3 respectively. Purified M13 RF DNA from each of these mutated t-PA genes was prepared from *E. coli* JM 101 cells. Subsequently, DNA fragments containing the mutated t-PA DNA sequence were used to construct expression vectors for the mutated t-PA.

50 ng of a synthetic oligonucleotide was phosphorylated for 30 min at 37° C. in 10 μl of 50 mM Tris-HCl pH 7.5, 10 mM MgCl$_2$, 10 mM dithiothreitol, 1 mM ATP containing 8 U of T4 polynucleotide kipase. For use as a probe, 400 ng of the synthetic oligonucleotide was phosphorylated as above except that ATP was replaced with 60 mCi [$\gamma^{32}$-P]-ATP (3000 μCi/mmol) resulting in approximately 50 to 60×10$^6$ cpm/400 ng of 24-mer. For heteroduplex formation, 10 ng single stranded M13mp8PABglII was heated to 95° C. (10 min), and slowly cooled to room temperature (30 min) in 40 μl 10 mM Tris-HCl pH 7.5, 10 mM MgCl$_2$, 1 mM dithiothreitol containing 10 ng of the phosphorylated primer and 50 ng of EcoRI-digested M13mp8PAB-glIIRF large fragment. Primer extension was started by the addition of 10 μl ligase buffer containing 2 mM ATP, 0.25 mM each of dGTP, dTTP, dCTP and dATP, 5 U of *E. coli* DNA polymerase I large fragment and 400 U of T4 DNA ligase. After 1 hr at 12° C. the reaction mixture was used to transform *E. coli* JM 101 cells.

Transformation was accomplished by mixing 10 μl of the ligation mixture with 200 μl of competent JM 101 cells, followed by incubation for 30 min on ice and 5 min at 37° C. Then 3.5 ml 2 YT top agar at 55° C. was mixed with 300 μl saturated JM 101 cells, 10 μl IPTG (200 mM) and 50 μl Xgal and after addition of the transformed cells plated on 9 cm Petri dishes containing LB with no drugs.

Colorless placques were picked and transferred to microtiter dish containing 100 μl 2 YT medium. The inoculated microtiter fluids were stamped on 15 cm diameter LB agar plates overlayed with a lawn of 600 μl JM 101 cells in 8 ml 2 YT top agar and incubated overnight at 37° C. The formed plaques were transferred to a nitrocellulose disc by physical contact for 1 min. The nitrocellulose disc was treated with 0.5M NaOH, 1.5M NaCl for 3 min and washed twice with 3M NaCl-0.5M Tris HCl pH 7.5 for 15 min and then with 2× SSC for 15 min. Prehybridization mix contains 10 mM Tris pH 7.5, 5 mM EDTA, 0.9M NaCl, 1X Denhardt 0.5 percent NP40, 100 μM ATP, 1 mM sodium pyrophosphate, 1 mM sodium phosphate and 50 μg/ml E. coli tRNA. 1 X Denhardt's contains per liter 200 mg Ficoll, 200 mg polyvinylpyrrolidone, 200 mg bovine serum albumin (BSA; fraction V). The disc was baked at 80° C. in vacuo for 90 min. The disc was then incubated for 3 hrs with 6 ml prehybridization fluid in a Petri dish followed by addition of 5×10$^6$ cpm labeled primer and hybridized overnight. Selective washing of the disc was performed with 0.4× SSC at 49° C. and after air-drying the disc was exposed to X-ray film. Positively hybridizing clones were further analyzed by dideoxy sequencing. See Aldeman, Ibid.

Figure 4:
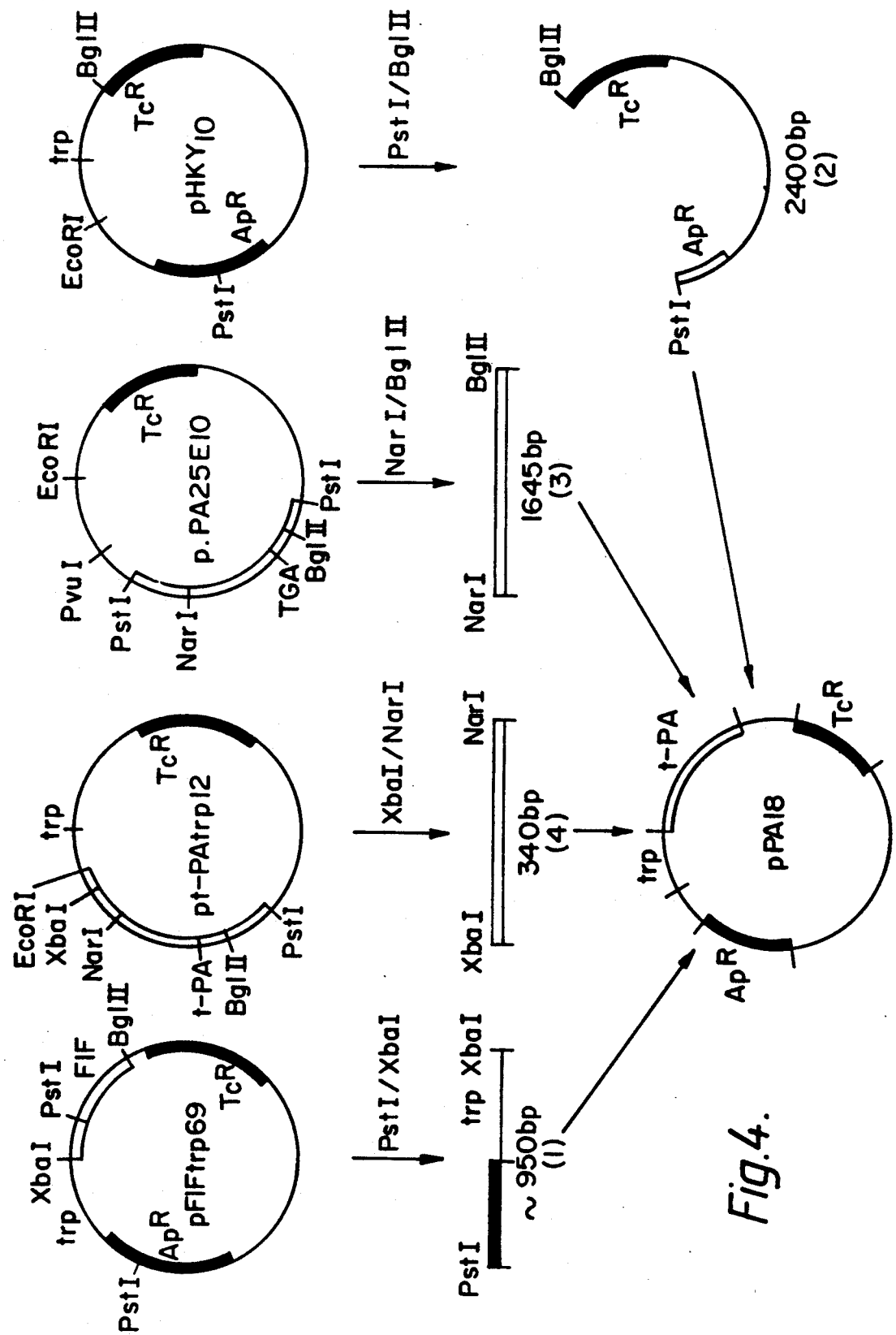
FIGS. 4 through 8 depict the construction of pXAP-PA18 3'ΔX10trpR.
Figure 5:
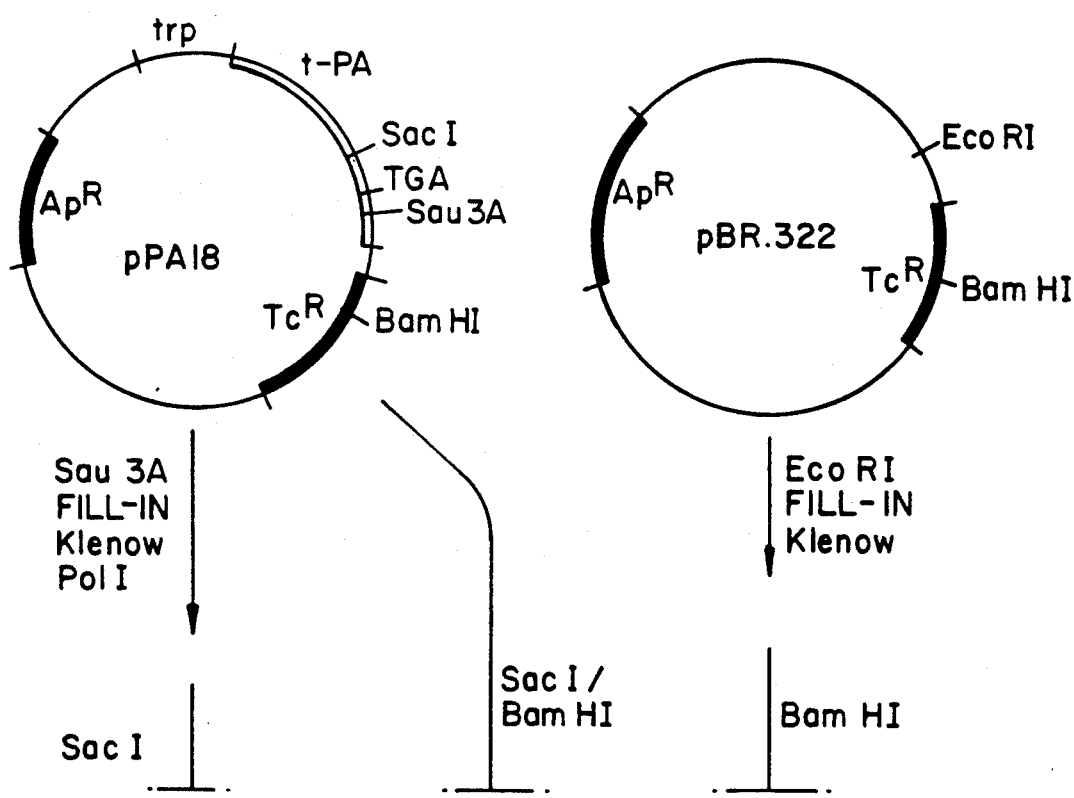
Figure 5:
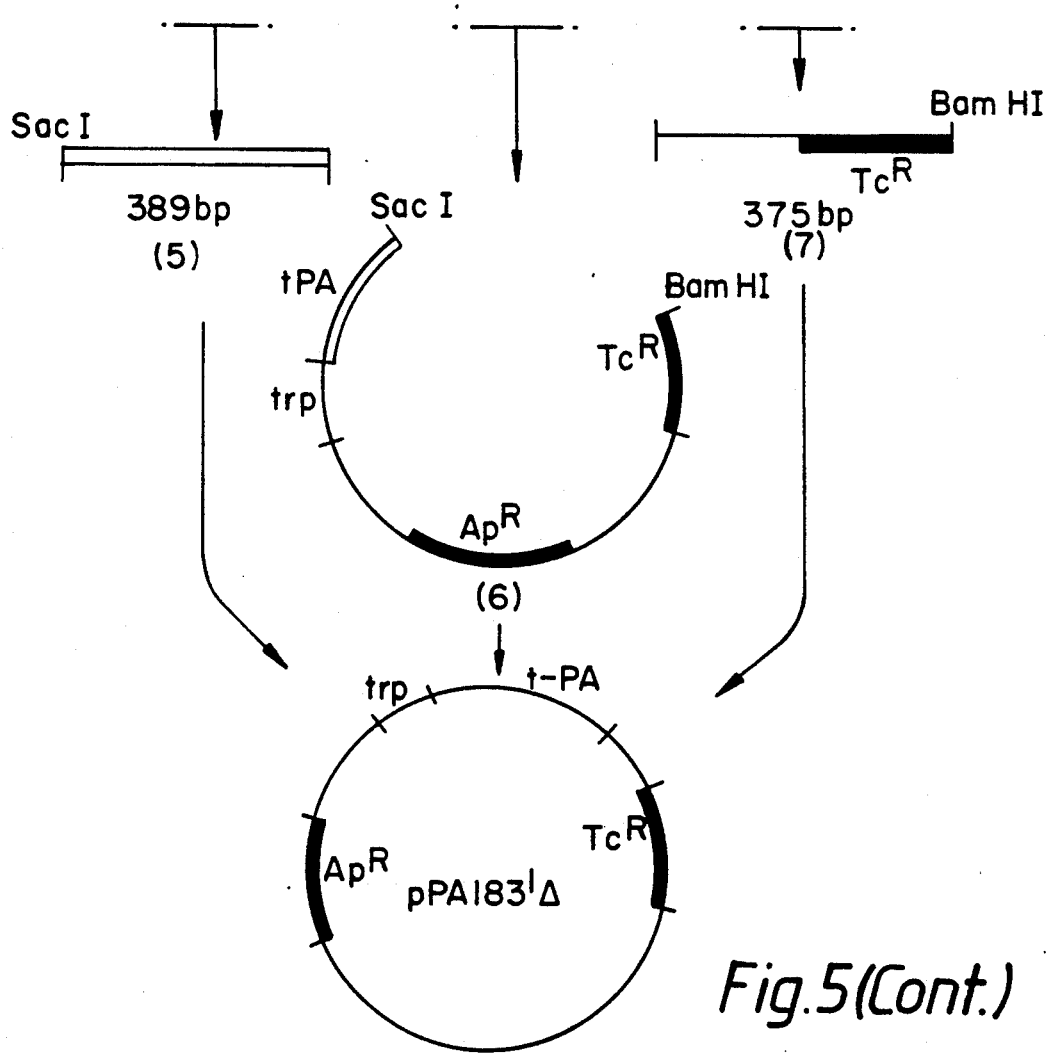

4. Construction of Vectors for Expression of Mutant t-PA E. coli pXAPPA18 3'Δx10trpR The plasmid pXAPPA18 3'Δx10trpR plasmid was constructed for use as an expression vector for the various mutated t-PA DNA sequences. The overall scheme used for construction of this plasmid is depicted in FIGS. 4 through 8. The resulting plasmid is depicted in FIG. 8. It contains the trpR repressor gene and a deletion of pBR322 DNA sequences which inhibit plasmid amplification. This deletion, known as XAP deletion, consists of the removal of 641 base pairs of pBR322 DNA sequences between the AvaI and PvuII restriction sites of pBR322 as disclosed by Sutcliff, Cold Spring Harbor Symposium on Quantitative Biology, Vol. 43, 77 (1979) Cold Spring Harbor Press, incorporated herein by reference. The trpR repressor gene compensates for the premature derepression of t-PA expression caused by increased plasmid copy number. Intermediate to the construction of pXAPPA18 3'Δ10trpR is the plasmid pPA18 which was constructed as depicted in FIG. 4. This plasmid contains the entire pre-t-PA structural gene as well as 5' and 3' on untranslated regions. A trp promoter associated with the t-PA gene and sequences conferring ampicillin and tetracycline resistance are also characteristic of this plasmid.

In order to construct pPA18, four plasmids were used, namely pFIFtrp69, pHKY10, ptPAtrp12 and pPA25E10. Plasmid pFIFtrp69 is disclosed in Goeddel et al., *Nucleic Acids Res.* 8, 4057 (1980). Plasmid pHKY10 is disclosed in U.S. patent application Ser. No. 685,521 filed Dec. 24, 1984 which is a continuation of U.S. Ser. No. 307,473 filed Oct. 1, 1981 which is a continuation of Ser. No. 133,296 filed Mar. 24, 1980, all now abandoned. U.S. Pat. No. 4,663,283 corresponds in text to the European patent application referred to in the following parenthetical text. (European Patent Application Publication No. 0036776). Plasmids ptPAtrp12 and pPA25E10 are disclosed in Pennica et al., *Nature* 301, 214 (1983), and in EPO Publication No. 093,619 supra.

Generally, the plasmid pFIFtrp69 is digested with PstI and XbaI to produce the 950 base pair fragment designated fragment 1 in FIG. 4. The plasmid ptPAtrp12 was digested with XbaI and NarI. From this the 340 base pair sequence designated fragment 4 in FIG. 4 was isolated. The plasmid pPA25E10 was digested with NarI and BglII. From this was isolated the 1604 base pair fragment designated fragment 3 in FIG. 4. The plasmid pHKY10 was digested with PstI and BglII to produce a 2900 base pair fragment designated fragment 2 in FIG. 4. These four fragments were ligated and this DNA used to transform E. coli cells to give pPA18.

The plasmid pPA18 was isolated and digested with Sau3A followed by treatment with the Klenow fragment of DNA polymerase I to fill in the restriction site. The non-circular plasmid was treated with SacI and a 389 base pair sequence designated fragment 5 in FIG. 5 was isolated. Plasmid pPA18 was also digested with SacI and BamHI. From this the vector fragment 6 was isolated. The plasmid pBR322, Boyer et al. *Gene* 2, (1977), was digested with EcoRI followed by treatment with the Klenow fragment of DNA polymerase I. This open-ended DNA sequence was treated with BamHI to produce the 375 base pair sequence depicted as fragment 7 in FIG. 5. Fragments 5, 6 and 7 were ligated and this preparation used to transform E. coli from which the plasmid pPA183'Δ was obtained. This plasmid is equivalent to pPA18 except that part of the 3' untranslated region of the t-PA gene has been removed.

Figure 6:
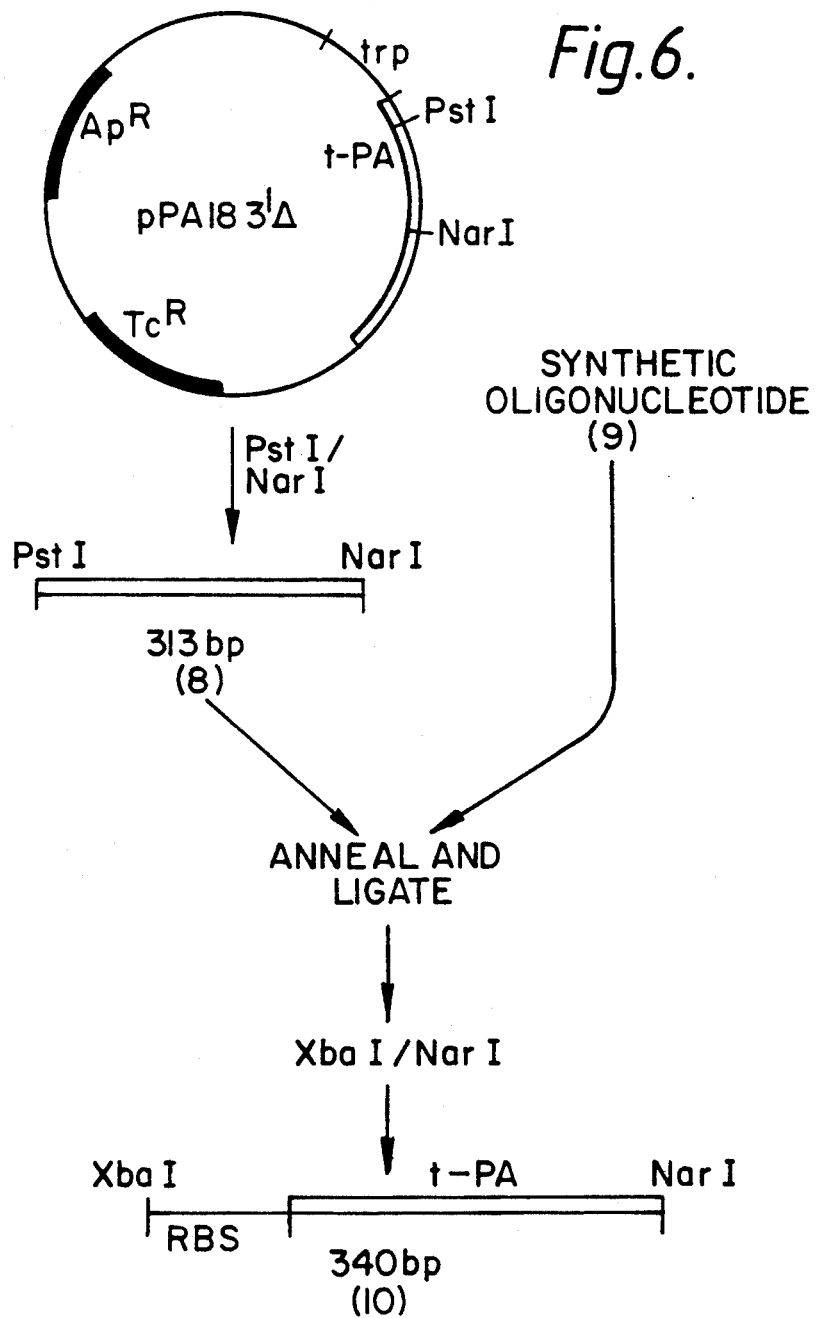

The plasmid pPA183'Δ was digested with PstI and NarI to produce a 313 base pair fragment designated fragment 8 in FIG. 6. This fragment encodes amino acids 8 through 109. Synthetic oligonucleotide fragment 9 has the following sequence:

```
5' CTAGAATTATGTCTTATCAAGTTATTTGCA
     TTAATACAGAATAGTTCAATAA      5'
```

This synthetic DNA was ligated to the PstI site of fragment 8 to regenerate the arginine codon at position 7 and the first six amino acid codons of the mature t-PA molecule. In addition, a ribosome binding site was positioned 5' to the synthetic N-terminal methionine codon positioned immediately 5' to residue 1 of the mature t-PA amino acid coding sequence. The 5' end of this oligonucleotide contains an XbaI restriction site. Thus, fragment 8 was ligated in the presence of the synthetic oligonucleotide fragment 9 and the mixture treated with XbaI and NarI to give fragment 10 (see FIG. 6).

Figure 7:
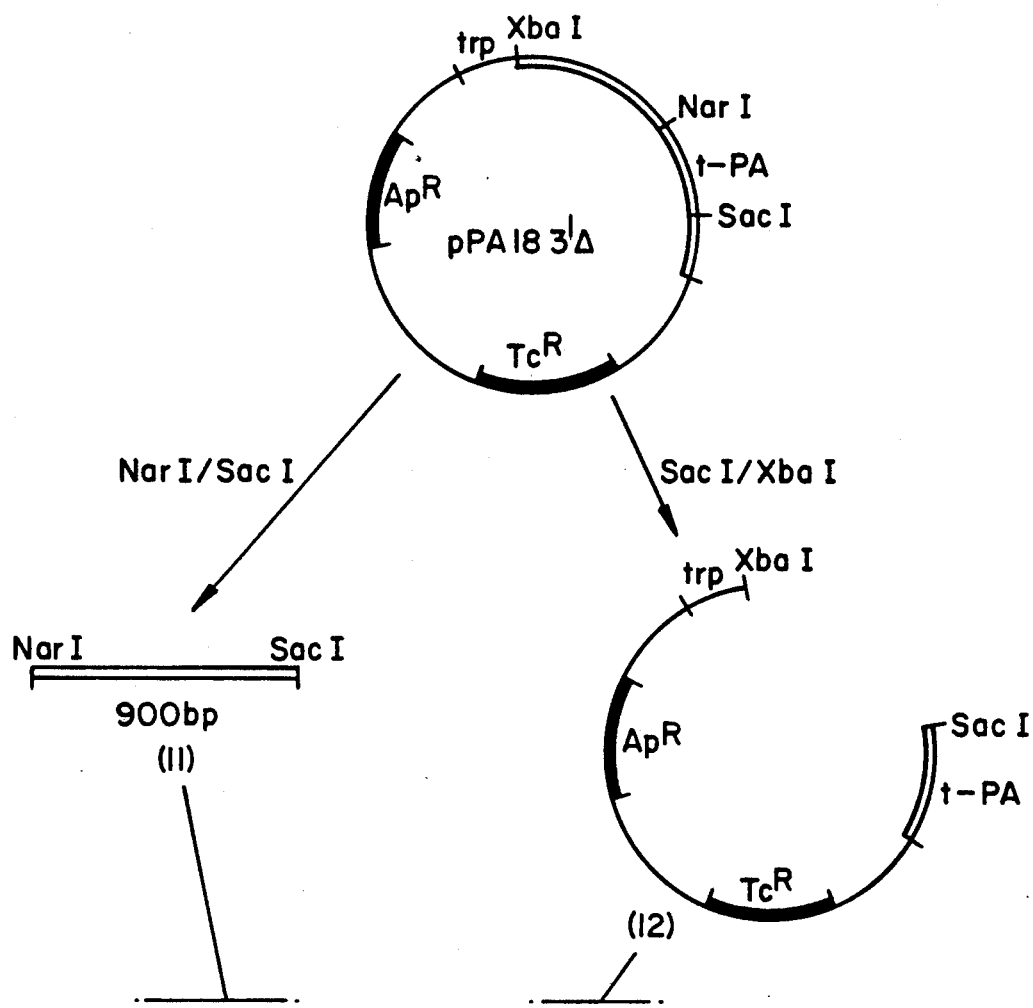
Figure 7:
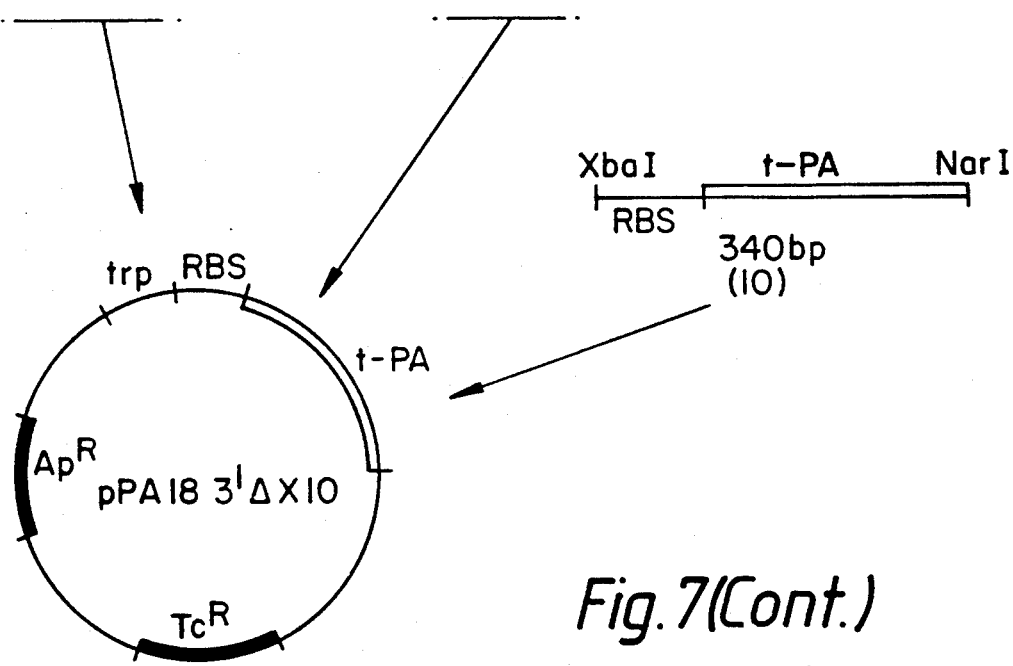
Figure 8:
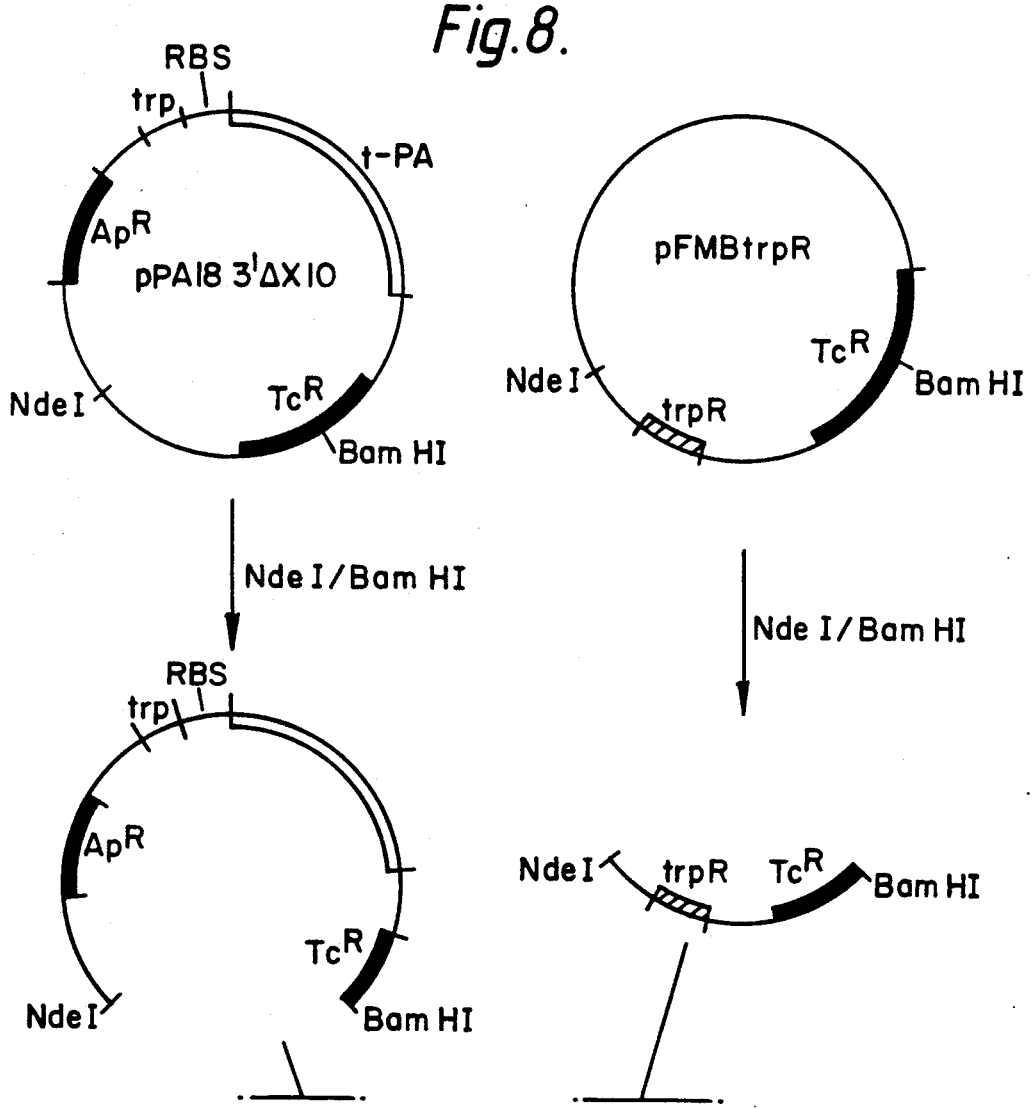
Figure 8:
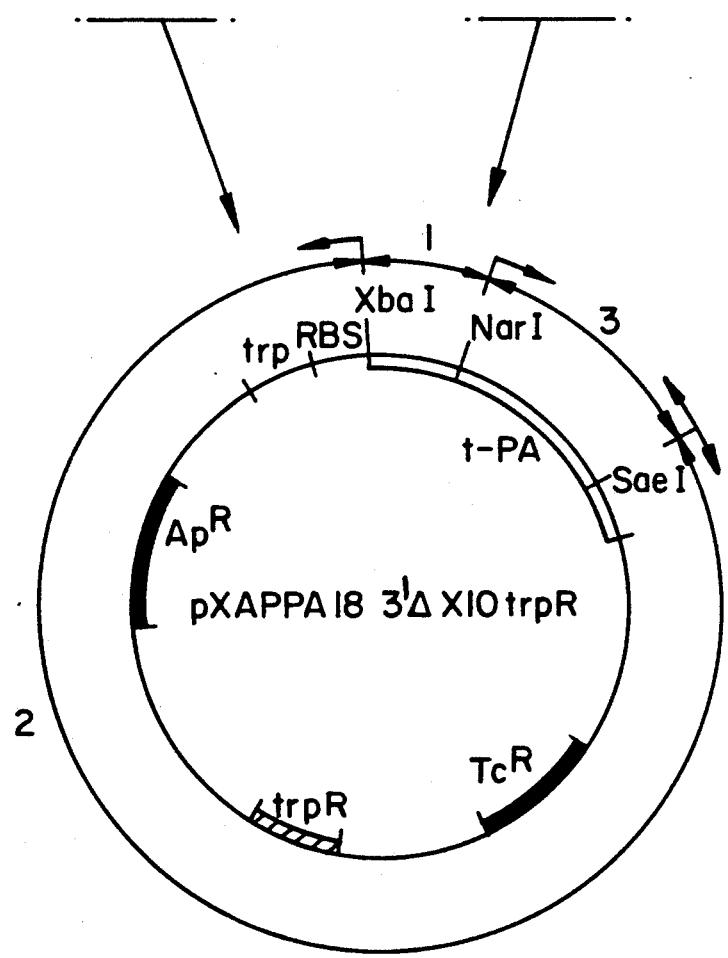

Plasmid pPA183'Δ was digested with NarI and SacI to produce the 900 base pair sequence designated fragment 11 in FIG. 7. This plasmid was also digested with SacI and XbaI to produce vector fragment 12 in FIG. 7. Fragment 10, 11, and 12 were ligated and used to transform E. coli from which was isolated pPA183'ΔX10. A DNA sequence containing the XAP deletion and trpR repressor gene is derived from pFMBtrpR which is disclosed in U.S. patent application Ser. No. 538,730 filed Oct. 3, 1983 now abandoned (EPO Publication No. 136907). Briefly, this plasmid was constructed from three plasmids known to those skilled in the art: phGH107, described in EPO Publication No. 022242, published Jan. 14, 1981, was used as a source for the lac inducible promoter; ptrpR3, described in Roeder et al., *Molecular Genetics* 176, 361 (1979) was used as the source of the coding sequence for trp repressor and pFMB1, described in EPO Publication No. 0068693 published Jan. 5, 1983, was used as the source of the coding sequence for the FMD antigen derived from strain A24.

To obtain the trp repressor sequence, ptrpR3 was treated with HaeIII, and the 334 base pair fragment was isolated from a 6 percent acrylamide gel and the isolated fragment was ligated with 16-mer EcoRI linkers having the sequence:

5'CCATAGAATTCTATGG.

To obtain vector backbone and the lac promoter, phGH107 was first digested with EcoRI, and treated with bacterial alkaline phosphatase. The large vector fragment containing the lacUV5 promoter was then ligated to the tailored trpR plasmid using T4 ligase, and the ligation mixture transformed into *E. coli*. Plasmid DNA from transformants was isolated and the presence of the desired plasmid, designated ptrpR/hGH 107, confirmed. Messing et al., *Nucleic Aids Res.* 9, 309 (1981).

ptrpR/hGH107 was partially digested with EcoR1, blunt ended using Klenow, treated with PvuII to provide the lac promoter/trp repressor operon (the 530 b.p. fragment). Partial PvuII digestion of pFMB1 and isolation of vector fragment on 6 percent polyacrylamide provided the expression vector backbone containing the FMB coding sequence under control of the trp promoter. The ptrpR/hGH107 fragment was mixed with the pFMB1 PvuII digest and ligated with T4 ligase. The ligation mixture was then used to transform *E. coli* strain 294, and transformants used as a source of plasmid DNA. The resulting plasmid, pFMB/trpR was verified by miniscreen, and for orientation of the insert by AvaI-PvuII digestion. Plasmid pFMB/trpR was digested with NdeI and BamHI. The fragment containing the trpR repressor was isolated. Plasmid pPA183'ΔX10 was digested with NdeI and BamHI. The main vector fragment was isolated. This vector fragment and trpR repressor fragment from pFMB trpR were ligated and the DNA mixture used to transform *E. coli* from which the plasmid pXAPPA183'ΔX10trpR was isolated, as shown in FIG. 8.

5. *E. coli* Expression Vectors for t-PA Mutants

FIG. 8 depicts the pXAPPA183'Δx10trpR vector used to express t-PA and t-PA mutants in *E. coli*. As can be seen, the expression of the native t-PA structural gene is controlled by the trp promoter. Attention is directed to the XbaI, NarI and SacI restriction sites. Plasmid pXAPPA183'x10trpR was digested with NarI and XbaI. A 340 base pair fragment identified as fragment 1 in FIG. 8 was isolated. A vector fragment identified as fragment 2 in FIG. 8 was obtained by isolating the large fragment obtained by digestion of pXAPPA183'Δx10trpR with XbaI and SacI. Fragment 3 (900 bp) was obtained by digesting with NarI and SacI RF DNA of each of the mutant t-PA M13 clones, obtained by site specific mutagenesis. (FIG. 3). Vectors expressing different mutant t-PAs were obtained by ligating fragments 1 and 2 with the fragments 3 and used to transform E. coli from which were isolated each of the *E. coli* mutant t-PA expression vectors:

pXAPPA183'Δx10trpR1B8 pXAPPA183'Δx10trpR2C9 pXAPPA183'Δx10trpR4A10 pXAPPA183'Δx10trpR3A7 pXAPPA183'Δx10trpR4B3

These plasmids, as well as the wild type t-PA expression vector pXAPPA183'Δx10trpR were used to transform *E. coli* W3110fhuA⁻.

*E. coli* W3110 fhuA⁻ is a T1 phage resistant bacterium characterized by a deletion or inversion of DNA sequences associated with the fhuA gene as disclosed in co-pending U.S. patent application Ser. No. 06/673,955 filed Nov. 21, 1984, now abandoned. Briefly, *E. coli* W3110 (ATTC 27325) is transduced with lambda bacteriophage containing the transposable element Tn10 which confers tetracycline resistance. Strains of Tn10 transduced W3110 are selected for resistance to phage infection. Phage resistant strains are pooled and infected with bacteriophage P1. The resulting lysate is used to transduce *E. coli* AT982 (Bukhari et al., *J. Bacteriology* 105, 844 (1971)). Strain AT 982 contains a Dap mutation located close to the fhuA gene. Accordingly, transduction of strain AT982 by the P1 lysate and selection of transductants which are tetracycline resistant and which regenerate the DAP function indicates that transposon Tn10 is located within the fhuA gene. Strains which are tetracycline resistant and demonstrate regenerated DA function are the source of DNA for bacteria phage P1 transduction of *E. coli* W3110. Transduced W3110 strains expressing tetracycline resistance and phage resistance are selected. These strains are then selected on the basis of resistance to phage infection and reversion to tetracycline sensitivity. Naloy et al., *J. Bacteriology* 145, 1110 (1981). The reversion to tetracycline sensitivity coupled with the retention of resistance to T1 phage infection indicates that DNA sequence associated with the fhuA gene have either been deleted or inverted irreversibly. Strains so constructed are designated *E. coli* W3110 fhuA⁻.

The phage containing the transposable element Tn10 which was used to insert Tn10 into W3110 was constructed as follows. The starting material was lambda cI857b 2210am29. This phage is known to those skilled in the art Kleckner, *J. Mol Biol.* 116, 125 (1977), and was constructed from three well-known mutants of lambda by standard procedures. A lysate of this lambda phage was prepared on the amber suppressor *E. coli* C600 (ATCC No. 23724) which had been manipulated by procedures known to those skilled in the art to also carry the Tn10 transposon. Kleckner et al., *J. Mol Biol.* 116, 125 (1977). This lysate was used to infect *E. coli* C600 (lambda CI857) which contains an amber suppressor and a lambda prophage carrying the cI857 genotype. Lysates of tetracycline resistant colonies were prepared by heat induction by growing the tetracycline resistant colonies first in broth at 32° C. and thereafter at 42° C. for 90 minutes. The lysate was then plated on *E. coli* C600 and replica plated. The plaques appearing on *E. coli* C600 were replica plated at 32° C. on *E. coli* C600 and *E. coli* W3102 sup+ (lambda imm434) which contains the heteroimmune prophage lambda imm434. Kleckner N. et al., *Genetics* 90, 427 (1978). Plaques appearing on the heteroimmune strain are plated onto tetracycline plates. Plaques appearing on these plates are capable of transducing tetracycline resistance and are used in the above-described method for generating E. coli W3110 fhuA−.

Native t-PA and mutant t-PA were obtained from 10 liter cultures of these cells transformed with the appropriate t-PA mutant t-PA plasmid. Expression was induced by tryptophan deficient media.

6. Expression Vectors for t-PA Mutants in Mammalian Cells

Figure 9:
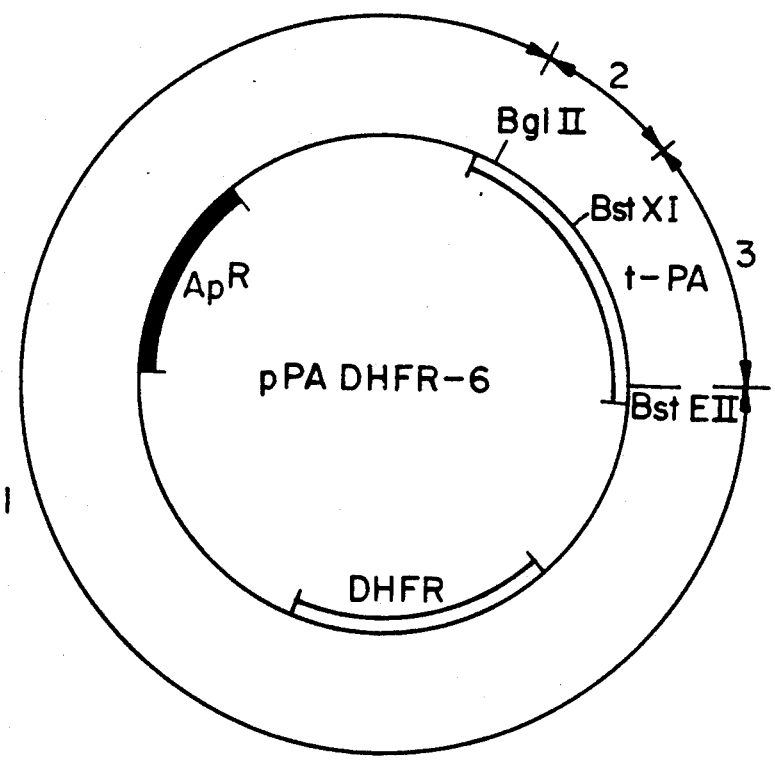
FIG. 9 depicts the plasmid pPADHFR-6 with relevant restriction sites.

The plasmid pPADHFR-6 (also designated pETP-FR—see EPO Application Publication No. 93619 supra) is depicted in FIG. 9. The expression of the native t-PA structural gene is under the control of the early promoter for SV40 T-antigen. This promoter also controls the expression of the DHFR gene. Attention is directed to the BglII, BstXI and BstEII restriction sites. Vector fragment designated as fragment 1 in FIG. 9 was obtained by isolating the large fragment generated by digestion of pPADHFR-6 with BglII and BstEII. The fragment designated as fragment 2 in FIG. 9 was obtained by isolating the 400 base pair t-PA fragment obtained from the digestion of pPADHFR-6 with BglII and BstXI. A 1,141 base pair t-PA fragment containing the desired mutations and corresponding to fragment 3 in FIG. 9 was obtained by digesting RF DNA from each of the mutant t-PA clones with BstXI and BstEII. Fragments 1 and 2 were ligated with each fragment 3. The DNA mixtures were used to transform E. coli. From each of the transformants, the respective eukaryotic expression vectors were obtained:

pPADHFR-6 1B8 pPADHFR-6 2C9 pPADHFR-6 4A110 pPADHFR-6 3A7 pPADHFR-6 4B3

These plasmids, as well as the non-mutated t-PA expression vector pPADHFR-6, were used to transfect DHFR deficient CHO cells as disclosed supra. (Graham et al., Virology 52, 456 (1973); see also EPO Publication No. 093619) Native and mutant t-PA expression was amplified by exposing cultures to increasing concentrations of methotrexate.

For example, plasmids pPADHFR-6 2C9 and pPADHFR-6 1B8 were used to transfect DHRF deficient CHO cells (Urlab & Chasin (PNAS 77, 4216 (1980)) using the calcium phosphate precipitation method of Graham et al., Virology 52, 46 (1973).

In each case, the colonies that arose in selective medium (medium lacking hypoxanthine, glycine, and thymidine (−HGT) were pooled and grown further in −HGT medium. These cells were plated at $2 \times 10^5$ cells per 100 mm plate in 20 nM methotrexate (MTX) to select for amplification of plasmid sequences. Five clones that grew in 250 nM MTX were extracted from the plate and all were found to be secreting t-PA into the medium. These clones were used for further study.

7. Preparation of Expression Plasmid pCisTPA

The vector pCIHt-PA containing the cytomegalovirus enhancer and promoter, the cytomegalovirus splice donor site and intron, the Ig variable region splice acceptor site, the cDNA encoding t-PA (Pennica et al., Nature 301, 214 (1983)) and the hepatitis surface antigen polyadenylation and transcription termination site was constructed.

The vector pF8CIS containing the cytomegalovirus enhancer (Boshart, M et al., Cell 41, 520 (1985)) and promoter (Thomsen, D. R. et al., 520 (1984)), the cytomegalovirus splice donor site and a portion of an intron (Sternberg, R. M. et al., J. of Virol. 49, 190–199 (1984)), the Ig variable region intron and splice acceptor site, the cDNA encoding factor VIII and the SV40 polyadenylation site was constructed. The three parts of the construction are detailed below.

1) The ampicillin resistance marker and replication origin of the final vector was derived from the starting plasmid pUC13pML a variant of the plasmid pML (Lusky, M. and Botchen, M. Nature 293, 79 (1981)). pUC13pML was constructed by transferring the polylinker of pUC13 (Veira, J. and Messing, J., Gene 19:259 (1982)) to the EcoRI and HindIII sites of pML. A second starting plasmid pUC8CMV was the source of the CMV enhancer, promoter and splice donor sequence. pUC8CMV was constructed by inserting nucleotides 1 through 732 for the DMV enhancer, promoter and splice donor sequence into the blunted PstI and SphI sites of pUC8. Veira, J. and Messing J. supra. Synthetic BamHI-HindIII linkers (commercially available from New England Biolabs) were ligated to the cohesive BamHI end creating a HindIII site. Following this ligation a HindIII-KincII digest was performed. This digest yielded a fragment of approximately 800 bp which contained the CMV enhancer, promoter and splice donor site. Following gel isolation this 800 bp fragment was ligated to a 2900 bp piece of pUC13pML. The fragment required for the construction of pF8CIS was obtained by digestion of the above intermediate plasmid with SalI and HindIII. This 3123 bp piece contained the resistance marker for ampicillin, the origin of replication from pUC13pML and the control sequences for the CMV including the enhancer, promoter and splice donor site.

2) The Ig variable region intron and splice acceptor sequence was constructed using a synthetic oligomer. A 99-mer and a 30-mer were chemically synthesized having the following sequence for the IgG intron and splice acceptor site (Bothwell et al., Cell 24, 625 (1981)):

```
 1  5'AGTAGCAAGCTTGACGTGTGGCAGGCTTGA...
31     GATCTGGCCATACACTTGAGTGACAATGA...
60     CATCCACTTTGCCTTTCTCTCCACAGGT...
88     GTCCACTCCCAG3'
 1  3'CAGGTGAGGGTGCAGCTTGACGTCGTCGGA5'
```

DNA polymerase I (Klenow fragment) filled in the synthetic piece and created a double stranded fragment. Wartell, R. M. and W. S. Reznikoff, Gene 9, 307 (1980). This was followed by a double digest of PstI and HindIII. This synthetic linker was cloned into pUC13 (Veira, J. and Messing, J., Gene 19, 259 (1982)) at the PstI and HindII sites. The clone containing the synthetic oligonucleotide, labelled pUCIg.10, was digested with PstI. A ClaI site was added to this fragment by use of a PstI-ClaI linker. Following digestion with HindIII and 118 bp piece containing part of the Ig intron and the Ig variable region splice acceptor was gel isolated.

3) The third part of the construction scheme replaced the hepatitis surface antigen 3' end with the polyadenylation site and transcription termination site of the early region of SV40. A vector, pUC.SV40 containing the SV40 sequences was inserted into pUC8 at the BamHI site described in Viera, J. and Messing, J., supra. pUC.SV40 was then digested with EcoRI and HpaI. A 143 bp fragment containing only the SV40 polyadenylation site was gel isolated from this digest. Two additional fragments were gel isolated following digestion of pSVE.8c1D. European Patent Publication No. 160457. The 4.8 kb fragment generated by EcoRI and ClaI digest contains the SV40-DHFR transcription unit, the origin of replication of pML and the ampicillin resistance marker. The 7.5 kb fragment produced following digestion with ClaI and HpaI contains the cDNA for factor VIII. A three-part ligation yields pSVE.8c24D. This intermediate plasmid was digested by ClaI and SalI to give a 9611 bp fragment containing the cDNA for factor VIII with and SV40 polyadenylation and transcription termination sites followed by the SV40 DHFR transcription unit.

The final three part ligation to yield pF8CIS used: a) the 3123 bp SalI HindIII fragment containing origin of replication, the ampicillin resistance marker and the CMV enhancer, promoter and splice donor; b) the 118 bp HindIII-ClaI fragment containing the Ig intron and splice acceptor; and, c) a 9611 bp ClaI-SalI fragment containing the cDNA for factor VIII, SV40 polyadenylation site and the SV40 DHFR transcription unit.

Next, the completion of the construction of plasmid pCIH t-PA from intermediate plasmid pCla t-PA and plasmid pF8CIS (above) was undertaken:

The t-PA cDNA was first cloned into pML to provide a ClaI site at the 5' end of the gene. To do this a 3238 bp HindIII fragment from pSVpa-DHFR (otherwise referred to as pETPFR, supra.) was inserted into the Hind III site of pML (Lasky et al., *Nature* 293, 79 (1981)). Colonies were screened for clones which have the 5' end of the cDNA juxtaposed to the ClaI site. The intermediate plasmid was labelled pClatPA. A t-PA cDNA followed by the 3' polyadenylation region was isolated as a ClaI-KpnI fragment of 2870 bp. This fragment was ligated to the 5146 bp fragment of pF8CIS. This ClaI-KpnI fragment of the CIS vector provided the 5' control region, a SV40-DHFR transcriptional unit, the ampicillin resistance gene and origin region from pML.

Expression levels of t-PA were obtained by transfecting CHO and 293 cells with pCIHt-PA.

The vector pCIStPA containing the cytomegalovirus enhancer and promoter, the cytomegalovirus splice donor site and intron, the Ig variable region splice acceptor site, the cDNA encoding tPA and the pSV40 polyadenylation sequence was finally constructed.

The starting vectors for this construction are pCIHtPA and pF8CIS. The latter vector has the same 5' controls as pCIHtPA but includes the cDNA for factor VIII and the SV40 polyadenylation site. KiNi was used to cleave 3' of the tPA cDNA. The resultant 3' overhang was blunted by T4 polymerase. pCIHtPA was then cut with ClaI. This site separates the chimeric intron cleaving between the CMV intronic sequences and the Ig variable region intron. An 2870 bp fragment was gel isolated from the ClaI treatment. The SV40 polyadenylation site, DHFR, transcription control, bacterial origin of replication and amp$^r$ gene, as well as the CMV enhancer and promoter and splice donor were isolated from pF8CIS. These elements were isolated into fragments as a 2525 bp SaI-BamHl fragment and a HpaI-Sal and 3113 bp fragment. A three part ligation of the KpNI(blunt)-ClaI fragment with the HpaI-Sal fragment and Sal to BamHl fragment yields pCIStPA, which was expressed in both CHO and 293 cells.

(Incorporated by reference herein is the relevant subject matter of U.S. Ser. No. 07/463,863 filed Jan. 5, 1990, which is a continuing application U.S.S.N. 07/071,674 filed July 9, 1987, now abandoned, which is a continuing application of Ser. No. 06/907,185 filed Sep. 12, 1986, now abandoned.)

8. Oligonucleotide Design

Several 23-mer oligonucleotides having the following sequences 5'-G-CCT-CAG-TTT-XYZ-ATC-AAA-GGA-G-3' where XYZ is, respectively,

| GCC | (ala) | A** | ATG | (met) | M |
|---|---|---|---|---|---|
| TGC | (cys) | C | AAC | (asn) | N |
| GAC | (asp) | D | CCC | (pro) | P |
| TTC | (phe) | F | CAG | (gln) | Q |
| CAC | (his) | H | AGC | (ser) | S |
| ATC | (ile) | I | AAC | (thr) | T |
| AAG | (lys) | K | GTG | (val) | V |
| CTG | (leu) | L | TGC | (trp) | W |
|  |  |  | TAC | (tyr) | Y |

**Single letter alphabet of amino acids (supra.)

** Single letter alphabet of amino acids (supra.)
were synthesized as above by the phosphotriester method of Crea et al., *Nucleic Acids Research* 8, 2331 (1980).

9. Construction of Recombinant M13 Template

Figure 13:
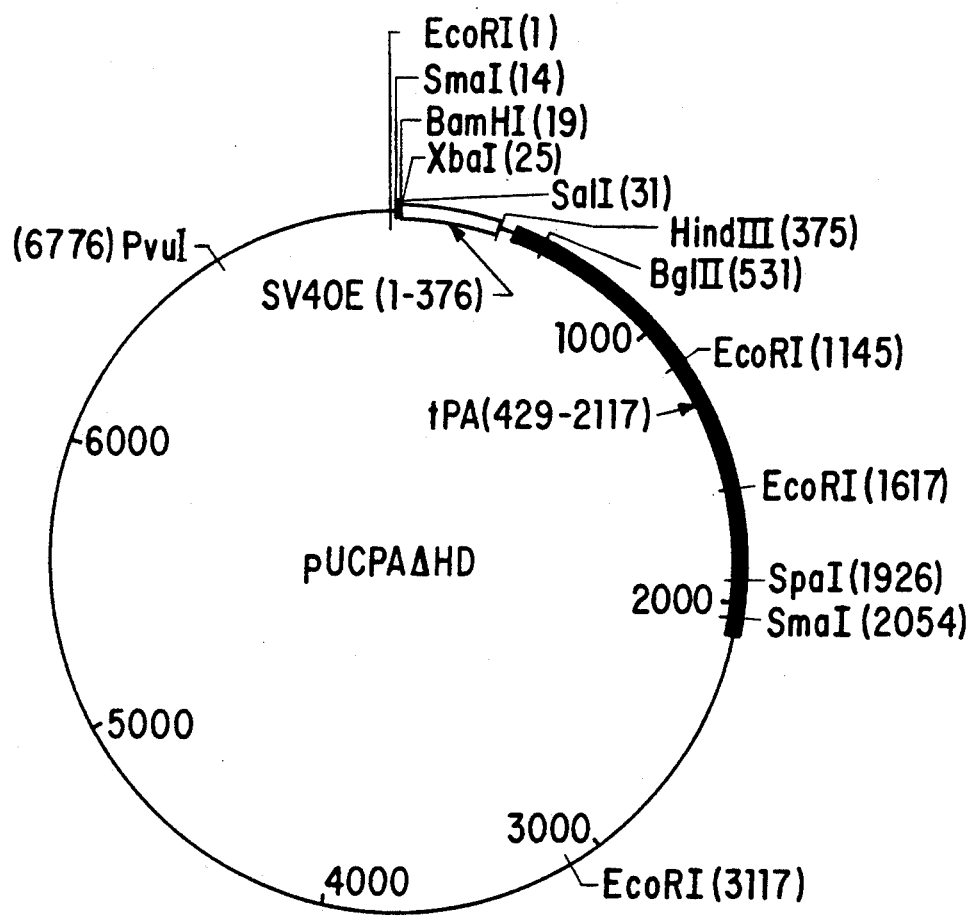
FIG. 13 depicts a restriction map of a starting plasmid pUCPAΔHD.
Figure 14:
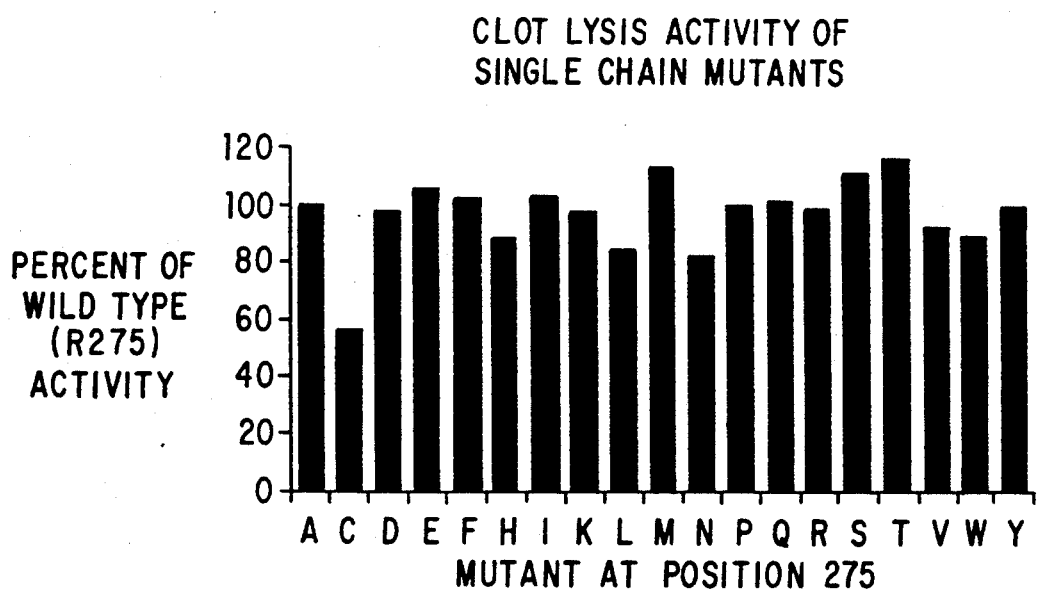
FIG. 14 is a graphic display of specific activities of various 275 mutants hereof in an in vitro clot lysis assay (ELISA used to determine protein concentration).
Figure 15:
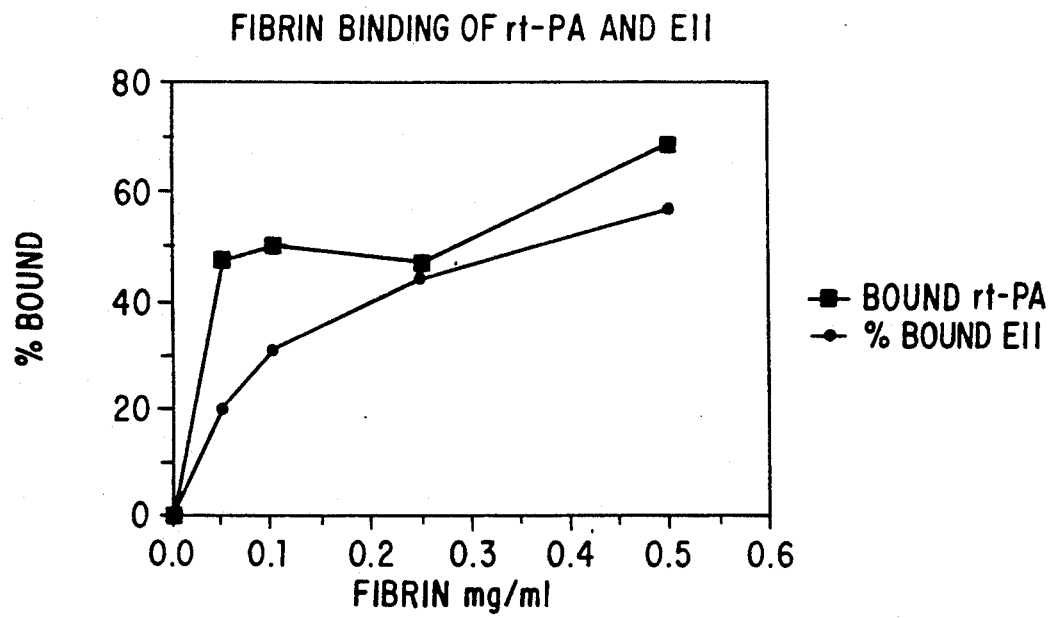
FIG. 15 is a graphic display of fibrin binding activity of E275I277 t-PA ("EII") versus wild-type t-PA ("rt-PA").
Figure 16:
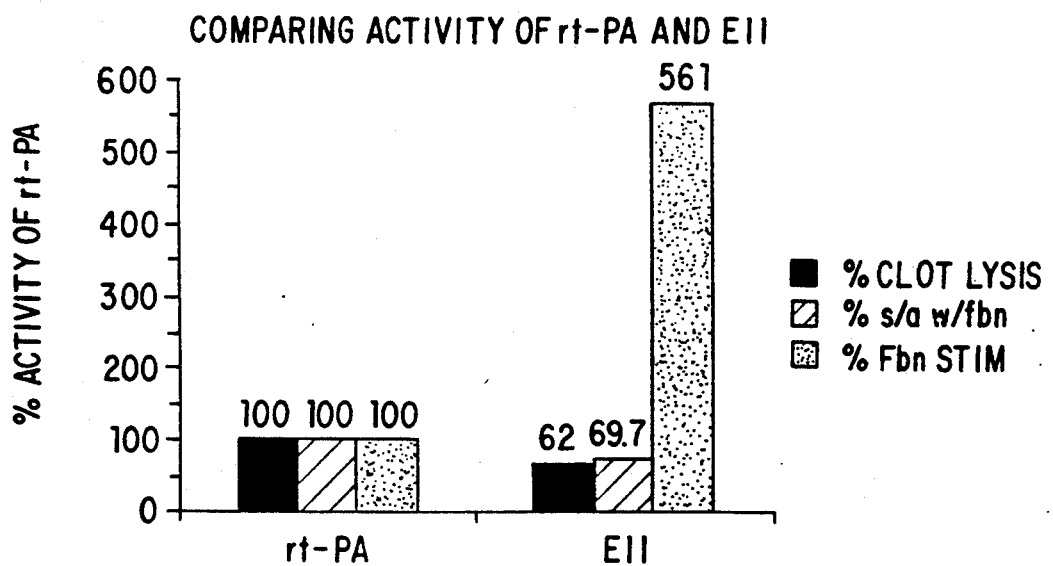
FIG. 16 is a graphic display comparing the activities of E275I277 t-PA ("EII") and wild-type t-PA ("rt-PA").

Plasmid pUCPAΔHD (FIG. 13) is a derivative of plasmid designated pETPFR (otherwise designated pPADHFR-6 disclosed in European Application No. 93619, supra), with the following modifications: 1) 166 bp of 5' untranslated DNA has been trimmed from the 5' end of the t-PA gene, using exonuclease Bal 31; 2) a Hind III site has been added to the new 5' end of the t-PA gene; 3) a polylinker, containing recognition sites for EcoRl, SacI, SmaI, BamHI, BaI, Sal I, and Pvu II, has been added to the 5' end of the SV40 early promoter that drives t-PA expression; 4) the Hind III site at position 3539 of pETPFR has been destroyed by a Klenow fill-in reaction.

Plasmid pUCPAAHD (FIG. 13) was digested with SmaI, and the ca. 2.0 kb fragment containing the t-PA gene through condon No. 507 was isolated by PAGE and electroelution of the fragment from the gel. M13mp10 (Messing, *Methods in Enzymology* 101, 20 (1983)) vector was also digested with SmaI extracted once with phenol, chloroform, ethanol precipitated, and re-suspended in 50 MMtris pH8.0, 1mMEDIA (TE). The ca. 2.0 kb fragment from pUCPAAHD was ligated into the SmaI cut M13mp10 using T4 DNA ligase and the resulting DNA was used to transform *E. coli* JM101. The resulting phage was isolated and the presence of the insert was verified and its orientation determined by restriction analysis of phage minipreps. One recombinant phage, M13/t-PA-SMA, was chosen as template for subsequent mutagenesis.

10. Mutagenesis Reaction

The several oligonucleotides (23-mers) prepared as described above in Paragraph 8. were separately annealed to singlestranded M13/t-PA-SMA DNA, and treated with *E. coli* DNA polymerase Klenow fragment in the presence of dNTPs and T4 DNA ligase to create in vitro heteroduplex RF molecules, as described by Adelman et al., DNA 2, 183 (1983). These molecules were used to transform *E. coli* strain JM101 (ATCC No. 33876) and phage incorporating the desired mutation were detected by plaque hybridization using the mutagenesis primer as a probe. (Adelman et al., DNA 2, 183 (1983). Mutant phage were isolated and contained the respective (XYZ) mutant DNA at position 275.

11. Subcloning the (XYZ) Mutants into Expression Plasmid pCistPA

Double stranded DNA of the respective (XYZ) mutants of Paragraph 10. above were digested with ScaI and ApaI and the fragments purified by PAGE. These fragments were then used in a three way ScaI-ApaI, SacII-ScaI ligation into pCistPA to replace the corresponding fragment in pCistPA.

Recombinant plasmids containing the t-PA gene fragment were identified and introduced into and expressed in human embryonic kidney (293) cells (Graham et al., *J. Gen. Virol.* 36, 59 (1977)) using generally available methods.

The t-PA mutants are obtained from the resulting cell line and are separated for use, preferably using a t-PA specific polyclonal antibody purification column.

E. Assay Methods

1. Mutant t-PA and t-PA Purification

The various t-PAs expressed in mammalian cells as described above were secreted into the cell culture medium. The medium containing such t-PAs was used directly in various assays to be described hereafter or was subjected to one or more of the following purification steps to increase the purity of t-PA or mutant t-PA prior to such assays.

Media from CHO cells containing mutant t-PA was batch extracted with chelating Sepharose (Pharmacia) (10-20 mL resin/L media) activated with zinc chloride as described by Rijken et al., *Biochim. & Biophys. Acta.* 580 140 (1979) and collected on a filter. The resin was poured into a column, washed with a buffer containing 0.02M sodium phosphate, pH 8.0, 0.25M NaCl, 0.01 percent TWEEN 80 and 10 mg/liter aprotinin. The t-PA was eluted with the same buffer containing 50 mM imidazole. The t-PA pool was dialyzed into 0.02M sodium phosphate, pH 8, 0.25M NaCl and 0.01 percent TWEEN 80 and loaded onto a lysine Sepharose resin, Radcliffe et al., *Arch. Biochem. Biohpys.* 189, 185 (1978) and Allen et al., *Thrombosis Heamostasis* 45, 43 (1981), or benzamidine Sepharose resin, Bykowska, et al., *Biochim. & Biophys. Acta*, 703, 113 (1982). The lysine-sepharose column was washed briefly with 0.02M sodium phosphate, pH 8, 1M NaCl and 0.01 percent TWEEN 80 and t-PA or mutant t-PA eluted with the same buffer containing 0.5M arginine. The benzamidine Sepharose was washed with the dialysis buffer and eluted with the dialysis buffer containing 1M guanidine. The resulting proteins were greater than 90% pure as analyzed by SDS-PAGE. In addition to the use of the foregoing purification techniques, a t-PA specific immobilized polyclonal antibody or immobilized monoclonal antibody column may be used (see, for example, Nielsen et al., *EMBO J.* 2, 115 (1983).

2. SDS Polyacrylamide Gel Electrophoresis (SDS-PAGE)

Samples of media containing t-PA protein or the t-PA mutant proteins were concentrated by vacuum and diluted into sodium dodecyl sulfate (SDS) sample buffer. Where indicated, 10 mM dithiothreitol (DTT) was added to reduce the protein disulfides. Discontinuous SDS electrophoresis using 10% or 7 to 17% polyacrylamide resolving gels was performed according to the procedure of Laemmli. [Laemmli et al., *Nature* 227, 680 (1970)]. For analysis of plasma samples, 4% to 10% SDS polyacrylamide gradient resolving gels were used with the buffer system of Laemmli. Estimated molecular weights (Mr) from SDS-PAGE analysis were obtained by comparison to the mobility of protein of known molecular weight.

3. Bubble Release Clot Lysis

Recombinant (non-mutant) t-PA and mutant t-PAs hereof (mutant t-PA) were assayed for their ability to solubilize fibrin clots by the bubble release clot lysis assay.

Briefly, thrombin (Sigma Chemical Co.) was dissolved in distilled water to approximately 1000 units/ml. This stock solution was diluted 1:30 with assay buffer which contained 0.06M monobasic sodium phosphate, 0.06M dibasic sodium phosphate, 200 mg/liter sodium azide and 0.01% TWEEN 80. A series of test tubes containing 0.5 ml of diluted thrombin (30-40 units/ml) and 0.5 ml of either various concentrations of t-PA (16 ng/ml to $1 \times 10^6$ ng/ml); appropriate controls or unknown sample in appropriate dilutions were prepared. A second series of test tubes containing 20 µl plasminogen (1.0 mg/ml), and 1.0 ml of fibrinogen (1 mg/ml) and 10 µl of hollow glass microspheres greater than 45 mesh (3M Company) was also prepared.

The above reagents and test tubes were kept on ice until the final step of the assay. 200 µl of either the thrombin-t-PA or thrombin-mutant t-PA solutions were added sequentially to a test tube containing the plasminogen, fibrinogen, and microspheres, vortexed for 15 seconds and placed in a 37° C. water bath. Clots formed in each tube within 30 seconds. The time between t-PA addition and the endpoint of the reaction was measured. The endpoint was defined as the time when the microspheres in the assay had risen to the surface.

The amount of thrombolytic activity of a particular sample was determined by reference to s standard t-PA curve. Specific activity was calculated based on the amount of t-PA or mutant t-PA present as determined by radioimmunoassay.

4. In Vitro Clot Lysis Assay

Recombinant t-PA and mutant t-PA were also assayed in an in vitro clot lysis system.

Briefly, human blood was collected with 3.13% sodium citrate as anticoagulant and the cellular fraction removed by centrifugation. 50 µl of 0.5M $CaCl_2$ 25 µl bovine-thrombin (100 units/ml) and 10 µl of human $^{125}I$-fibrinogen (100,000 cpm/10 µl) was added to each ml of plasma. This plasma mix was aspirated into silicon tubing with an inside diameter of 4 mm and incubated at 37° C. for 1 hour. Segments (1 cm) of the tubing were cut and the clot removed. The clots were placed in buffer consisting of 0.3M NaCl, 0.02M sodium citrate, pH 5, and 0.01% TWEEN 80. The clots were rinsed four times in one hour with fresh buffer. The amount of radioactivity in the last rinse did not exceed about 10% of the amount of radioactivity in the clot. Each clot was placed in 2.5 ml of plasma. A 250 µl sample of plasma was taken as a zero point. A sample of t-PA or mutant t-PA was added in a volume of 100 µl. Samples (250 µl)

were taken at 1, 2, 3 and 4 hours and the radioactivity contained therein determined. Standards containing 5, 10, 20 and 40 units of t-PA activity per ml were run in parallel. The percent lysis was calculated after correction for volume changes after each sample.

5. Chromogenic Assays

S-2288: t-PA may be measured directly using the Kabi synthetic tripeptide chromogenic substrate, S-2288 (Helena Laboratories, Beaumont, Tex.). For this assay, t-PA and 1 mM S-2288 (final concentration) in 0.05 M Tris, pH 7.4 containing 0.012 M NaCl and 0.01 percent TWEEN 80 were incubated at 37° C. for 10 minutes. The reaction was stopped by the addition of 50 µl of glacial acetic acid to 0.5 ml reaction mixture. The activity was calculated from the absorbance at 405 nm using the following equation, standardized by the manufacturer:

$$\frac{\text{Activity in 0.5 ml reaction mixture}}{\text{(IU, international units)}} = \frac{\Delta OD \times 793.65 \; OD}{\text{time of incubation}} \; \text{IU-min}$$

S-2251: Plasminogen activation by t-PA was measured using the Kabi specific tripeptide chromogenic substrate specific for plasmin, S-2251 (Helena Laboratories). An aliquot of the sample was mixed with 0.10 ml of 0.7 mg/ml plasminogen (0.05M Tris, pH 7.4 containing 0.012 m NaCl) plus 0.02 ml of human fibrinogen 20 mgs/ml (0.05M Tris HCl, pH 7.4, containing 0.012M NaCl) and the volume adjusted to 0.15 ml. The mixture was incubated at 37° C. for 10 minutes, 0.35 ml of S2251 (0.86 mM solution in above buffer) was added, and the reaction continued for 5 or 10 minutes at 37° C. Glacial acetic acid (50 µl) was added to terminate the reaction and the absorbance at 405 nm was measured. Quantitation of the amount, of activity was obtained by comparison to the results obtained using a recombinant native t-PA sample which had been standardized using the S-2288 assay. This was necessary initially because the absorbance at 405 nm varied from day to day as the plasminogen aged and also changed if different preparations of plasminogen and fibrinogen were used. This variability was ultimately reduced by careful preparation of large amounts of human plasminogen (glu-plasminogen) with subsequent lyophilization of aliquots of the material. The aliquots were stored at −20° C. Prior to use, the redissolved plasminogen preparations were stored at 0° C. for not more than 4 hours. Stimulation of t-PA activity by fibrinogen was measured by comparing the activity of solutions containing high concentrations of fibrinogen to similar reaction mixtures in which fibrinogen has been omitted. Due to the insolubility of fibrin, fibrinogen was used in this assay. The stimulation by high concentrations of fibrinogen appears to mimic the stimulation that would be expected by the insoluble fibrin.

6. In vivo Inhibitor-Complex Assay

Recombinant t-PA and mutated t-PA were assay in vitro to determine their reactivity with naturally occurring inhibitors of t-PA activity. Generally, t-PA and mutant t-PA were iodinated with $^{125}$I by using Iodobeads (Pierce Chemical Co.) resulting in t-PA or mutant t-PA having specific radioactivities approximately $2 \times 10^6$ cpm/µg. For in vitro complex formation, the radiolabeled t-PA (1 µg) was added to freshly drawn citrated human whole blood (500 µl). The samples were incubated at room temperature and the reaction stopped by dilution of an aliquot into 2% SDS. Samples were analyzed in 4 to 10% polyacrylamide gradient SDS-PAGE. Complexes were detected by autoradiography.

7. Fibrin Binding Assay

Figure 11:
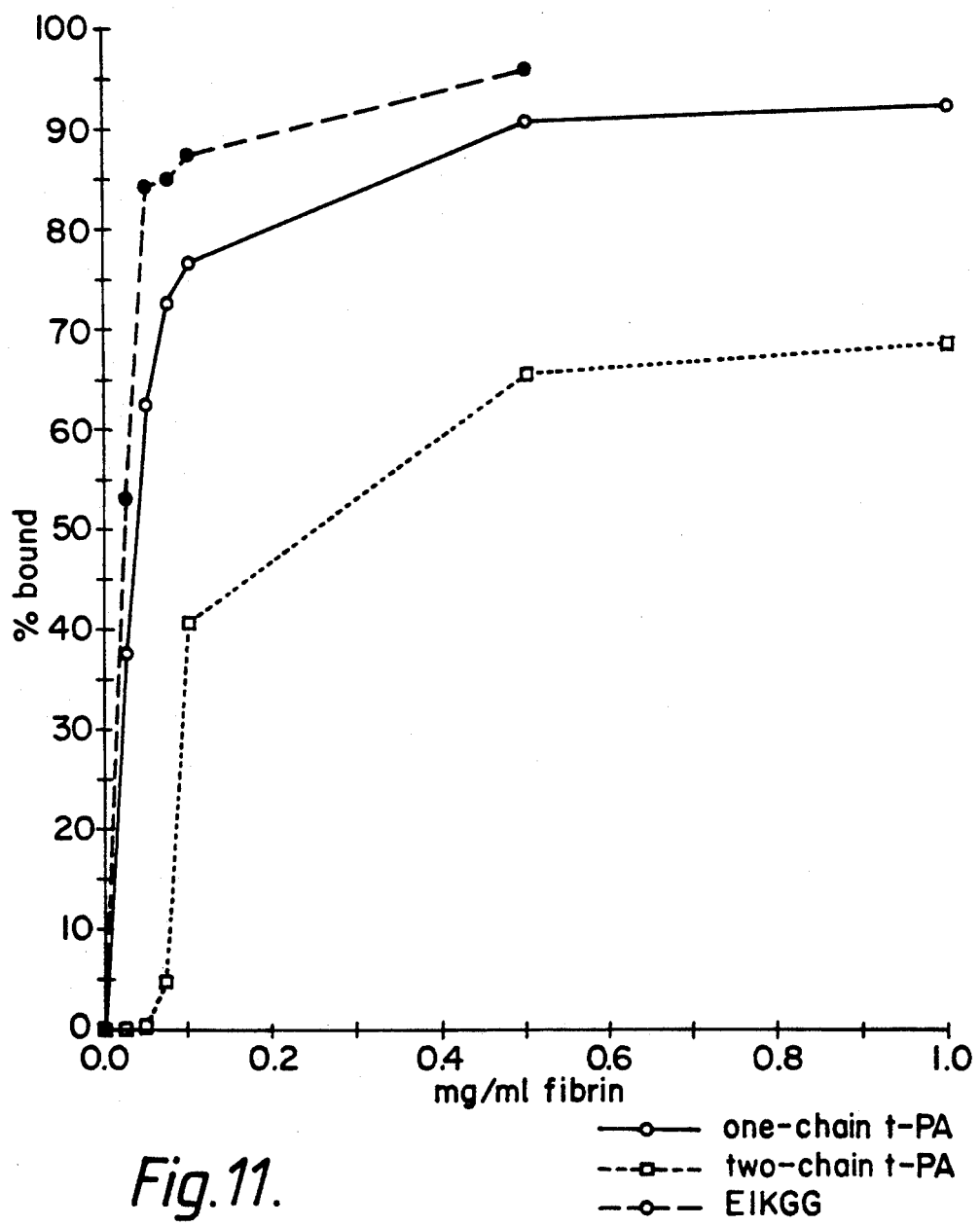
FIG. 11 shows the fibrin binding properties of one-chain t-PA, two-chain t-PA and of the mutated one-chain t-PA (EIKGG).

The method for fibrin binding is a modification of the method described by Rijken et al., *J. Biol. Chem.* 257, 2920 (1982). The t-PA sample to be tested (500 ng) is added to a solution containing 0.05M Tris, pH 7.4, 0.12M NaCl, 0.01% TWEEN 80, 1 mg/ml human serum albumin, and various concentrations of plasminogen free fibrinogen (0, 0.025, 0.05, 0.075, 0.1, 0.5 and 1.0 m/ml). The final volume of the reaction mixture is 1 ml. The sample is incubated at 37° C. for five minutes, followed by the addition of 1 unit of thrombin. The samples are incubated for one hour at 37° C. The clot is removed using a glass rod, and the amount of t-PA remaining unbound in the supernatant is determined. The data is plotted as percent t-PA bound versus the fibrinogen concentration (FIG. 11).

8. In Vivo Clot Lysis

The in vivo clot lysis model of Collen et al., *J. Clin. Invest.* 71, 368 (1983), was used. Male New Zealand white rabbits between 2.5 and 3 kg were anesthetized with ketamine, the jugular vein was catheterized and small communicating vessels in the region were ligated. Approximately 2 cm of the jugular was isolated with reversible ligatures, a thread was passed from the proximal to the distal end of the segment, the segment was flushed with a saline thrombin solution and filled with fresh rabbit blood which contained $^{125}$I human fibrinogen. After 30 minutes blood flow was resumed across the clot. The t-PA i.v. infusion was started with an initial bolus of 10% of the total dose. The infusion was delivered over 4 hours. Thirty minutes after the end of the infusion the clot was harvested and counted. The recovery of radioactivity was used as a quality control; blood samples, urine, swabs and syringes were counted to assure that the estimate of the mount of radioactivity present in the initial clot was accurate.

F. Assay Results t-PA mutants with the following sequences at the two-chain activation site, residues 270 through 279, have been expressed in both *E. coli* and Chinese Hamster Ovary cells (CHO cells):

|  | 275 | 279 |  |  |
|---|---|---|---|---|
| Native | —Arg—Ile—Lys—Gly—Gly— | (RIKGG) | (t-PA) |
| 1B8 | —Gly—Ile—Lys—Gly—Gly— | (GIKGG) | (G275 t-PA) |
| 2C9 | —Glu—Ile—Lys—Gly—Gly— | (EIKGG) | (E275 t-PA) |

1. Western Blots and Zymography

The EIKGG & GIKGG mutants expressed in CHO cells were analyzed by Western blots derived from reduced and non-reduced SDS-PAGE gels. Native single-chain t-PA shows up as two bands having molecular weights of 52,000 and 50,000 daltons due to a difference in the extent of glycosylation. The EIKGG mutant from a non-reduced SDS-PAGE showed one major immunoreactive band at a molecular weight of approximately 50,000 daltons. The Western blot of the mutant GIKGG from a non-reduced SDS-PAGE, however, showed a molecular weight of 55,000 daltons. The difference in apparent molecular weight of the GIKGG mutant as compared to native t-PA may indicate a slightly different conformation or carbohydrate structure compared to native t-PA, perhaps attributable to a conformational aberration due to a presumed presence of a second, adventitious mutation at amino acid 261 (cys to tyr). Cleavage of the protein at arg 275 can be detected by a lower molecular weight of t-PA when analyzed following reduction (thereby separating the protease and Kringle chains). Zymographs of the reduced SDS-PAGE gels showed that plasminogen activator activity in these samples was at the molecular weight of the immunoreactive band of the single-chain form of t-PA (approximately 60,000). The two-chain form of t-PA has an electrophoretic mobility consistent with a molecular weight of approximately 30,000 daltons. The other 275 (XYZ) mutants prepared as described above appear as single bands when subjected to both reduced and unreduced SDS-PAGE, except $Lys_{275}$ which showed a lower molecular weight band following reduction. This procedure demonstrated that single-chain forms of the mutant t-PA proteins, with the single exception, were present in the media from transformed cells.

S-2251 Assay

Analysis of the native and a mutant EIKGG t-PA by the S-2251 assay is shown in Table I. These values were obtained prior to the use of glu-plasminogen in the assay in order to decrease assay variability. The naturally occurring t-PA sequence RIKGG was assigned an arbitrary specific activity in the presence of fibrinogen on the basis of the S2288 assay. This standard t-PA was assayed with each of the EIKGG t-PA mutants to normalize results.

As can be seen the EIKGG t-PA mutant, regardless of the degree of purification, has a specific activity in the S2251 plus fibrinogen assay greater than that for the recombinant t-PA.

TABLE I

| Mutation | Mutant | S-2251 + Fibrinogen | S-2251 − Fibrinogen | Fibrinogen Stimulation |
|---|---|---|---|---|
| RIKGG[1] | native | 250,000[4] | 25,000 | 10.0 |
| EIKGG[1] | 2C9 | 1,000,000 | 3,400 | 290.0 |
| EIKGG[2] | 2C9 | 420,000 | 3,100 | 134.0 |
| EIKGG[3] | 2C9 | 520,000 | 7,000 | 74.0 |

[1]purified using zinc chelate lysine-agarose
[2]purified using zinc chelate and benzamidine agarose
[3]assayed with no purification
[4]assigned activity The data in Table IA were obtained using high quality, lyophilized, glu-plasminogen. With a more reproducible assay, the EIKGG mutant was found to be equal in activity in the S-2251 assay in the presence of fibrinogen. In the absence of fibrinogen, the mutant was still less active than native (Tables I and IA), demonstrating a greater specificity.

TABLE IA

| Mutation | Mutant | S-2251 + Fibrinogen | S-2251 − Fibrinogen | Fibrinogen Stimulation |
|---|---|---|---|---|
| RIKGG[1] | native | 250,000[2] | 17,600 | 14 |
| EIKGG[1] | 2C9 | 248,000 | 500 | 500 |

[1]purified using zinc chelate lysine-agarose
[2]assigned activity

The other 275 (XYZ) mutants prepared as described above were tested and found to exhibit activity comparable to the EIK mutant.

2. Bubble Release Clot Lysis and In Vitro Clot Lysis Assay

The bubble release clot lysis assay was used to determine the specific activity of recombinant t-PA and the purified ElKGG t-PA mutant. The activity of each of these t-PAs was determined by the procedures described above. The concentration of t-PA and EIKGG mutant t-PA was determined by radioimmunoassay. The results of this assay including specific activity are shown in Table II.

TABLE II

| Sample | I.D. | U/ml Activity | Protein Conc. mg/ml | Specific Activity |
|---|---|---|---|---|
| 1 | EIKGG* | 8440 | 0.088 | 95,909 |
| 2 | EIKGG* | 7698 | 0.088 | 87,477 |
| 3 | t-PA** | 5640 | 0.088 | 64,090 |

1) Frozen - thawed once
2) Frozen - thawed four times
*purified using zinc-chelate and benzamidine-agarose
**purified using zinc-chelate and lysine-agarose The bubble release clot lysis assay demonstrates that a one-chain mutant of t-PA, specifically the EIKGG mutant t-PA, has a specific activity 50% greater than recombinant t-PA. As can be seen repeated freezing and thawing resulted in a slight decrease in the specific activity of the EIKGG t-PA mutant. However, the mutant t-PA still maintained a specific activity greater than that of the recombinant t-PA.

Within the limits of assay reproducibility, and using more refined techniques (See Carlson et al., Anal. Biochem. 168, 428 (1988)), the other 275 (XYZ) mutants demonstrated clot lysis activity comparable to the EIK mutant, with the exception of CIK ($C_{275}$ t-PA) which showed a lower activity. In this assay, EIK (E275 t-PA) was about equivalent to wild-type (RIK) t-PA.

3. In Vivo Inhibitor-Complex Assay

Figure 10:
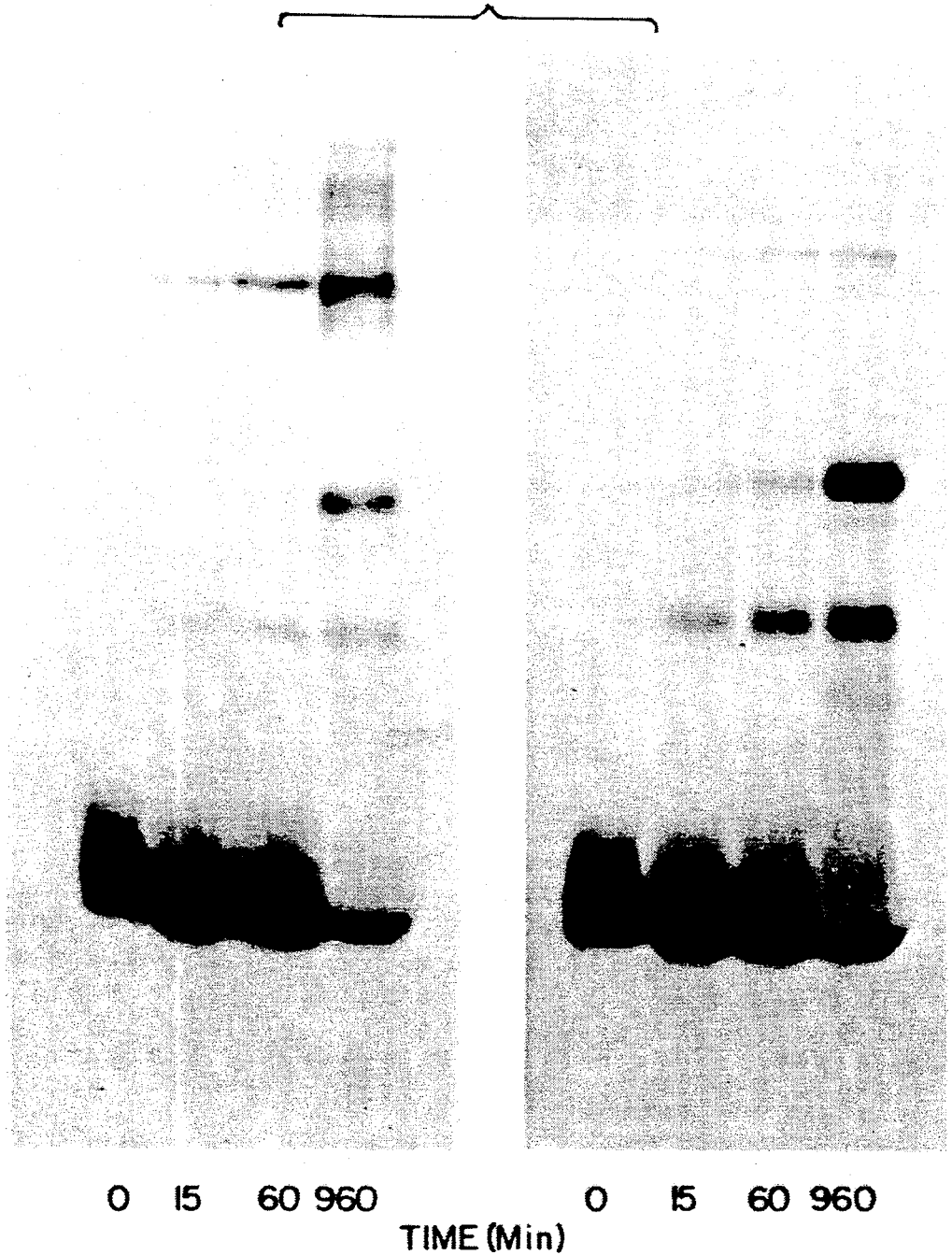
FIG. 10 depicts the plasma protease inhibitor complexes formed by radiolabeled t-PA (left panel) and EIKGG t-PA (right panel) as by autoradiography of an SDS-PAGE gel.

The inactivation of proteases by plasma protease inhibitors is a well-studied mechanism for inactivating serum proteases. The resulting complexes are stable to denaturation and can be assessed by electrophoresis on SDS-PAGE. In this procedure, radiolabeled t-PA is added to plasma or whole blood and the sample incubated at 37° C. The sample is subjected to SDS-PAGE followed by autoradiography. The detection of radiolabel at positions of Mr greater than free t-PA is an indication of the amount of t-PA protease inhibitor complex which has been formed. When analyzed in rat blood, t-PA was found to slowly form complexes with Mr greater than 200,000. After several hours of incubation, greater than 70% of the radiolabel could be detected in such complexes. In contrast, the mutated t-PA did not form these complexes; the bulk of the radiolabel detected by autoradiography remained at the position of free, uninactivated enzyme. When a similar analysis was performed in human blood, (FIG. 10) t-PA also formed such complexes, but in addition formed complexes of Mr between 100,000 and 200,000. As with the rat blood, the mutant t-PA formed markedly less inhibitor complexes with Mr greater than 200,000. The protease inhibitor complexes with Mr values between 100,000 and 200,000 were still present. These results indicate that the mutant is not inactivated by the proteinase inhibitor(s)

which form complexes with Mr values greater than 200,000. Species differences are noted in the reactivity of both t-PA and the mutated t-PA in the formation of complexes between 100,000 and 200,000.

4. Fibrin Binding

It has previously been reported that one-chain and two-chain 2 forms of t-PA have approximately equal affinity for fibrin (Rijken et al., *J. Biol. Chem.* 257, 2920 (1982). In the assay described herein, in contrast, a markedly higher affinity for fibrin was observed for the one-chain form of t-PA as compared to the two-chain form (FIG. 11).

All of the other 275 (XYZ) mutants had activities comparable to EIK in the fibrin binding assay. It was determined that the GIK (G275 t-PA) mutant, prepared as described above, exhibited lower specific activity in this assay compared with RIK, thought to be attributable to a conformational aberration due to presumed presence of a second, adventitious mutation at amino acid 261 (cys to tyr). The CIK and KIK mutants also displayed lower, than wild-type (RIK), activities thought due respectively to some misfolding and some 2-chain form present.

5. In Vivo Clot Lysis

Figure 12:
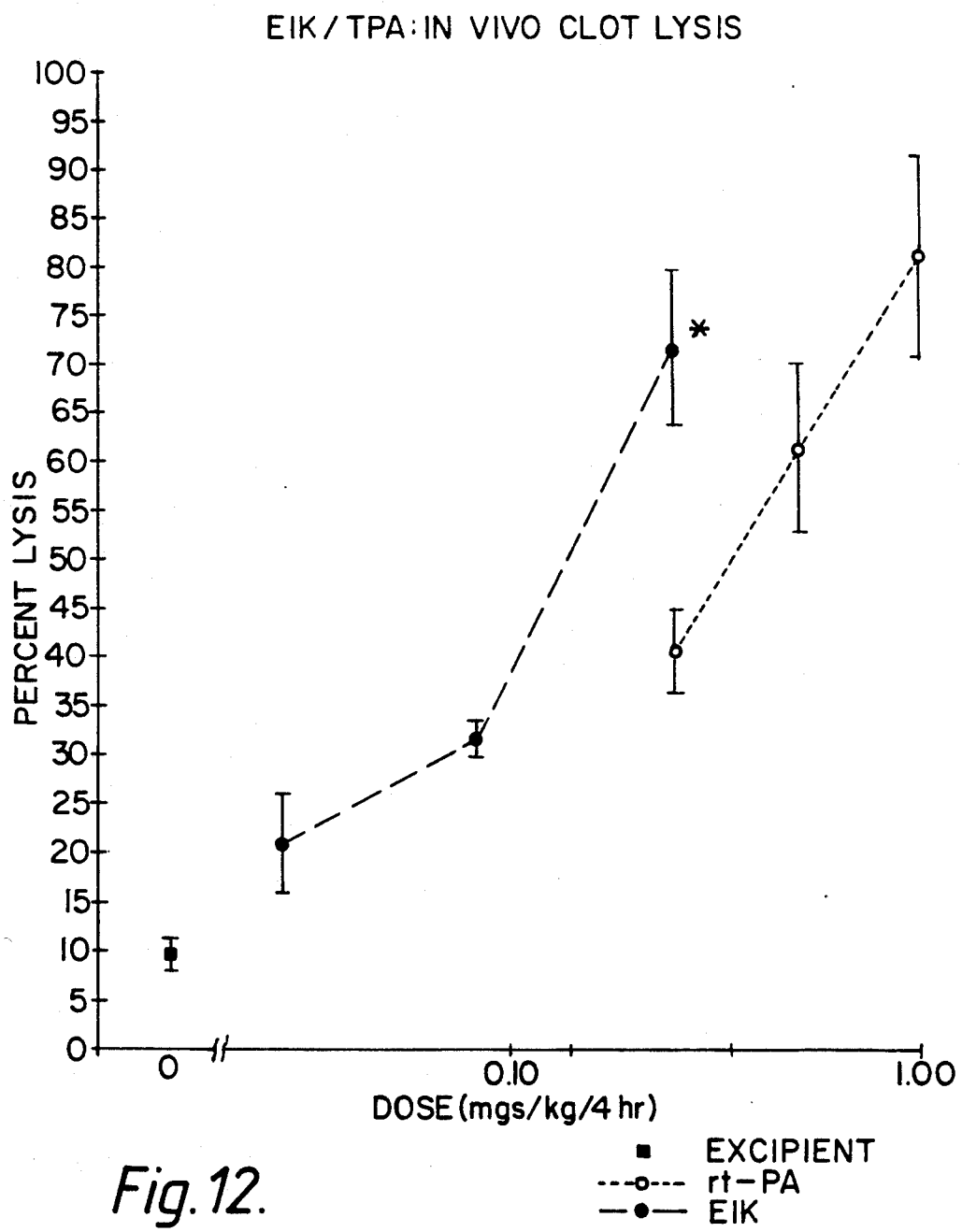
FIG. 12 depicts a dose-response curve of in vivo clot lysis (EIK is mutated one-chain t-PA; rt-PA is non-mutated t-PA).

FIG. 12 shows the relative dose response curves for t-PA (o) and the EIK mutant (o). The data are presented as the Mean$+/-$SEM with 5 rabbits in each group. The distance between the two curves at the 50% lysis point was measured and the potency of the EIK form of t-PA was estimated to be 2.4 times greater than the non-mutated form (RIK). A statistically significant difference was achieved at the 0.25 mg/kg dose ($p<0.01$).

G. Conclusion

The above results demonstrate that mutation at residue 275 of t-PA may be more efficacious than the natural form for two separate reasons:

1. Increased specificity: Assays of t-PA function indicate a more active/specific protein.
2. Decreased in vivo plasma inhibitor binding: in vivo inhibition of such mutants indicate a decrease in inactivation by certain protease inhibitors. This should allow for the circulation of the active uncomplexed form of t-PA thereby allowing for increased functional t-PA to dissolve a clot.

The scientific literature is contradictory on the enzymatic properties of the one-chain form of t-PA. In order to better understand the function of t-PA one can look to homologous proteins. Extensive investigations have been performed in the serine proteases trypsin and chymotrypsin. The t-PA protease domain is very similar to these proteins and is expected to function in a similar manner. Based on the mechanism of function determined for trypsin and chymotrypsin, preventing cleavage at arginine 275 of t-PA would be expected to affect only the functional characteristics of the protease domain. The increased fibrin affinity of the mutants is therefore surprising.

Regardless of the mechanism(s) involved (increased specificity, lack of protease inhibitor binding, increased affinity for fibrin, or combination of these), when one mutant was tested for its ability to lyse a blocked vein in vivo, it was found to be approximately 2.5 times more active than the t-PA of natural sequence. As discussed previously, the one-chain form of t-PA has been shown to be converted to the two-chain form at the site of a clot. Such a conversion would destroy any advantage associated with the one-chain form. Only a mutated form of t-PA is capable of being converted to the two-chain form by physiologic proteases will be able to preserve its advantages once at the site of a clot.

In addition, although consequent clot lysis activity was not apparently increased, pharmacokinetic data indicates that at equivalent dose rates, the EIK mutant gives plasma concentrations that are 1.7 fold higher in rabbits and 2.2 fold higher in monkeys than wild-type (RIK) t-PA.

Having described the preferred embodiment of the present invention, it will appear to those ordinarily skilled in the art that various modifications may be made to the disclosed embodiment, and that such modifications are intended to be within the scope of the present invention.

What is claimed is:

1. An isolated DNA sequence encoding a human tissue plasminogen activator (t-PA) in which position 275 is substituted by an amino acid other than arginine.

2. A DNA sequence according to claim 1 encoding $Glu_{275}$ human tissue plasminogen activator.

3. A DNA sequence according to claim 1 wherein position 277 is substituted by an amino acid other than lysine.

4. A DNA sequence according to claim 3 encoding $Glu_{275}$ $Ile_{277}$ human tissue plasminogen activator.

5. A replicable expression vector capable, in a transformant host cell, of expressing the DNA sequence according to claim 3.

6. A replicable expression vector capable of expressing the DNA sequence of claim 1 in a transformed host cell.

7. A microorganism transformed with the vector of claim 6.

8. A cell culture transformed with the vector of claim 6.

9. A mammalian cell culture transformed with the vector of claim 6.

10. The cell culture of claim 9 obtained by transforming a Chinese Hamster Ovary cell line.

11. A cell culture transformed with the vector according to claim 5.

12. The cell culture of claim 11 obtained by transforming a Chinese Hamster Ovary cell line.

13. A composition comprising a therapeutically effective amount of a human tissue plasminogen activator in which position 275 is substituted by an amino acid other than arginine in admixture with a pharmaceutically acceptable carrier.

14. A composition according to claim 13 wherein said human tissue plasminogen activator is $Glu_{275}$ human tissue plasminogen activator (E275 t-PA).

15. A composition according to claim 13 wherein said human tissue plasminogen activator is $Glu_{275}$ $Ile_{277}$ human tissue plasminogen activator (E275 I277 t-PA).

16. A method of treating thrombotic conditions in a subject comprising administering to said subject the composition of claim 13.

* * * * *